(12) United States Patent
Crowley et al.

(10) Patent No.: US 7,365,536 B2
(45) Date of Patent: Apr. 29, 2008

(54) PASSIVELY SHIELDED INDUCTIVE SENSOR SYSTEM FOR PERSONNEL SCREENING

(75) Inventors: Christopher Crowley, San Diego, CA (US); Daniel K. Lathrop, San Diego, CA (US)

(73) Assignee: General Electric Company, Schenectady, NY (US)

( * ) Notice: Subject to any disclaimer, the term of this patent is extended or adjusted under 35 U.S.C. 154(b) by 3 days.

(21) Appl. No.: 11/125,646

(22) Filed: May 10, 2005

(65) Prior Publication Data

US 2006/0255798 A1 Nov. 16, 2006

(51) Int. Cl.
*G01V 3/00* (2006.01)
(52) U.S. Cl. ........................ 324/300; 324/307
(58) Field of Classification Search ........ 324/300–322, 324/244, 228, 260; 600/410
See application file for complete search history.

(56) References Cited

U.S. PATENT DOCUMENTS

| | | | |
|---|---|---|---|
| 5,467,017 A | 11/1995 | Duerr et al. | |
| 6,194,898 B1 * | 2/2001 | Magnuson et al. | 324/300 |
| 6,771,064 B2 * | 8/2004 | Leibowitz et al. | 324/207.15 |
| 6,952,163 B2 * | 10/2005 | Huey et al. | 340/521 |
| 7,049,814 B2 * | 5/2006 | Mann | 324/300 |
| 7,154,266 B2 * | 12/2006 | Czipott et al. | 324/244 |
| 2004/0113781 A1 | 6/2004 | Stis | |
| 2004/0222790 A1 | 11/2004 | Karmi et al. | |
| 2005/0073307 A1 | 4/2005 | Manneschi | |
| 2006/0012366 A1 * | 1/2006 | Feldman et al. | 324/310 |

FOREIGN PATENT DOCUMENTS

EP 1526386 A1 4/2005
WO WO 99/21148 4/1999

OTHER PUBLICATIONS

"Company makes strides against shoe explosives", Bruce V. Bigelow, The San Diego Union Tribune, Feb. 25, 2004, 3 pp.
General Electric Company, PCT International Search Report, International Application No. PCT/US2006/016592; Feb. 28, 2007 (7 pgs.).
Geronimo E. Poletto, Tristan M. Osan & Daniel J. Pusiol; Article: Pulsed 14N NQR Device Designed to Detect Substances in the Presence of Environmental Noise; Title: Hyperfine Interactions Kluwer Academic Publishers Netherlands; Presented at the XVII International Symposium on Nuclear Quadrupole Interactions, Held in Bonn Germany 2004; vol. 159, No. 1-4, 2004, pp. 127-130.

* cited by examiner

*Primary Examiner*—Brij Shrivastav
(74) *Attorney, Agent, or Firm*—Eugene Hyun, Esq.; Armstrong Teasdale LLP

(57) ABSTRACT

An inspection system includes an electromagnetic shield having electrically conductive sidewalls spaced from one another. The shield also includes a conductive third wall which spans the distance between the sidewalls, and is electrically coupled to the sidewalls. The inspection system also has an inductive sensor positioned within the electromagnetic shield. The inductive sensor has two current branches, which exhibit anti-symmetric current flow. Typically, the two current branches are positioned on opposing sides of the medial plane of the electromagnetic shield.

28 Claims, 21 Drawing Sheets

PASSIVELY SHIELDED INDUCTIVE SENSOR SYSTEM FOR PERSONNEL SCREENING

BACKGROUND OF THE INVENTION

1. Field of the Invention

The present invention relates generally to an inspection system, and in particular to an inspection system for detecting explosives and other contraband using an inductive sensor employing anti-symmetric current branches.

2. Discussion of the Related Art

Presently, the detection of explosives and other contraband may be accomplished using inspection and detection systems implementing a variety of different technologies including nuclear quadrupolar resonant (NQR), nuclear magnetic resonance (NMR), metal detection, and the like. In prior NQR testing systems, for example, a sample is placed within a radio frequency (RF) coil and is typically irradiated with pulses or sequences of pulses of electromagnetic radiation having a frequency which is at or very close to one or more resonance frequencies of the quadrupolar nuclei in a substance which is to be detected. If the substance is present, the irradiating energy will generate a precessing magnetization which can induce voltage signals in a detection coil adjacent the sample at the resonance frequency, and which can be detected as a free induction decay during a decay period after each pulse, or as an echo after two or more pulses.

Conventional inspection systems utilizing inductive sensors have employed various techniques for shielding the system from external noise. One technique is to completely enclose the sensor in an electrically connected and grounded box. Another technique which is commonly used for NQR sensors, is to position the sensor within an enclosure having a wave-guide tunnel positioned at the entrance and exit to the inspection system. While such configurations have enjoyed considerable success in many respects, their use has been limited for inspecting humans since some people are wary or uncomfortable about having to walk and stand in confined spaces.

BRIEF DESCRIPTION OF THE INVENTION

In accordance with an embodiment of the invention, an inspection system includes an electromagnetic shield having electrically conductive sidewalls spaced from one another. The shield also includes a conductive third wall which spans the distance between the sidewalls, and is electrically coupled to the sidewalls. The inspection system also has an inductive sensor positioned within the electromagnetic shield. The inductive sensor has two current branches, which exhibit anti-symmetric current flow. Typically, the two current branches are positioned on opposing sides of the medial plane of the electromagnetic shield.

BRIEF DESCRIPTION OF THE DRAWINGS

The above and other aspects, features, and advantages of the present invention will become more apparent upon consideration of the following description of preferred embodiments, taken in conjunction with the accompanying drawing figures, wherein.

DETAILED DESCRIPTION OF THE INVENTION

In the following detailed description, reference is made to the accompanying drawing figures which form a part hereof, and which show by way of illustration specific embodiments of the invention. It is to be understood by those of ordinary skill in this technological field that other embodiments may be utilized, and structural, electrical, as well as procedural changes may be made without departing from the scope of the present invention.

As a matter of convenience, many embodiments of the invention will be described in the context of a walkthrough inspection system implemented as part of a typical aviation security system. Particular reference will be made to a "person" that is screened for explosives and other threat objects. However, it is to be understood that the present invention is not so limited and that many other applications are envisioned and possible within the teachings of this disclosure. Examples of particular applications of a walkthrough inspection system that may also be implemented include seaports, public buildings, public transportation facilities, prisons, hospitals, power plants, court houses, office buildings, hotels, and casinos, among others.

Figure 1:
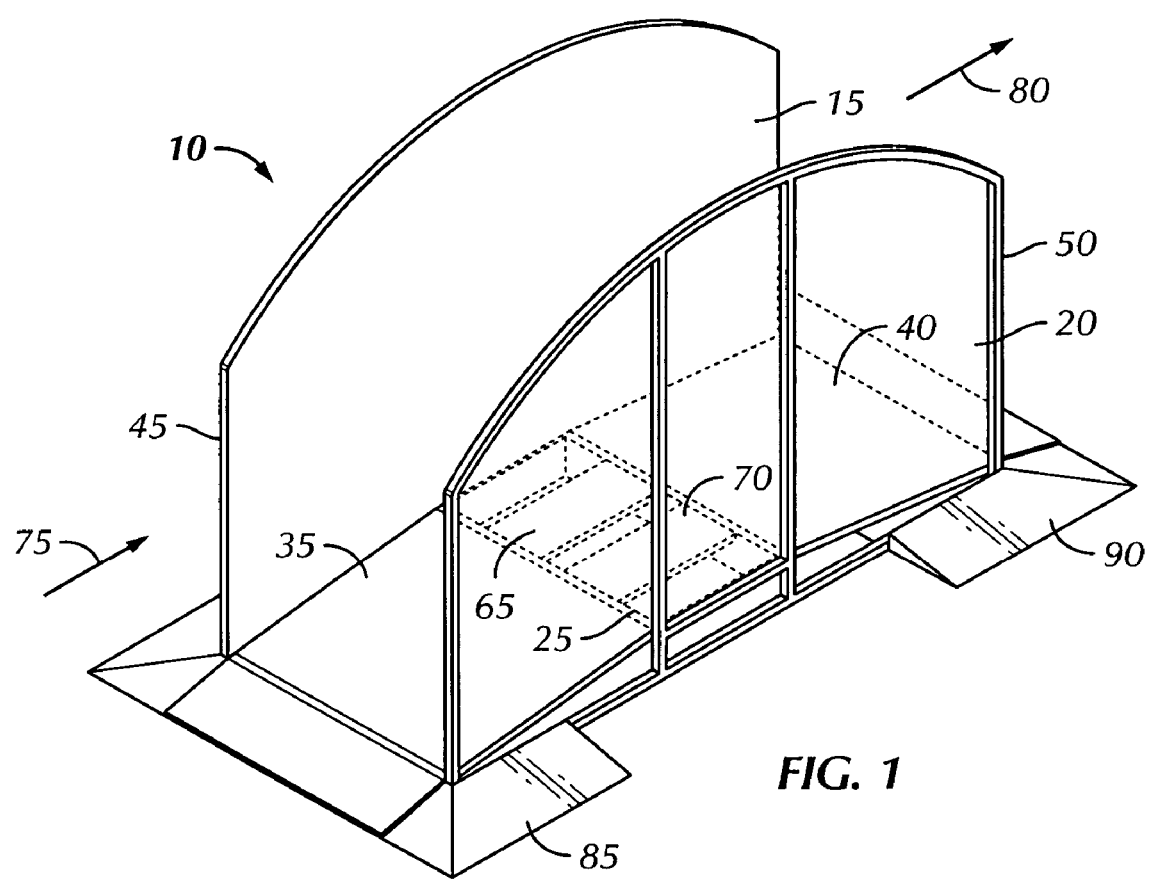
FIGS. 1, 2, and 3 are perspective, side, and end-views, respectively, of an inspection system in accordance with embodiments of the invention.
Figure 2:
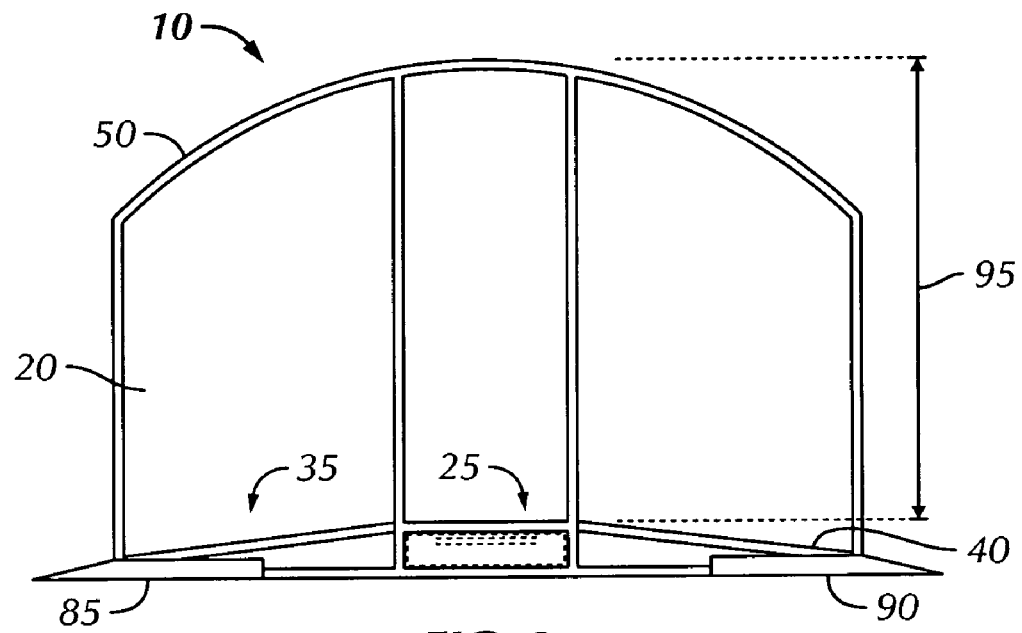
Figure 3:
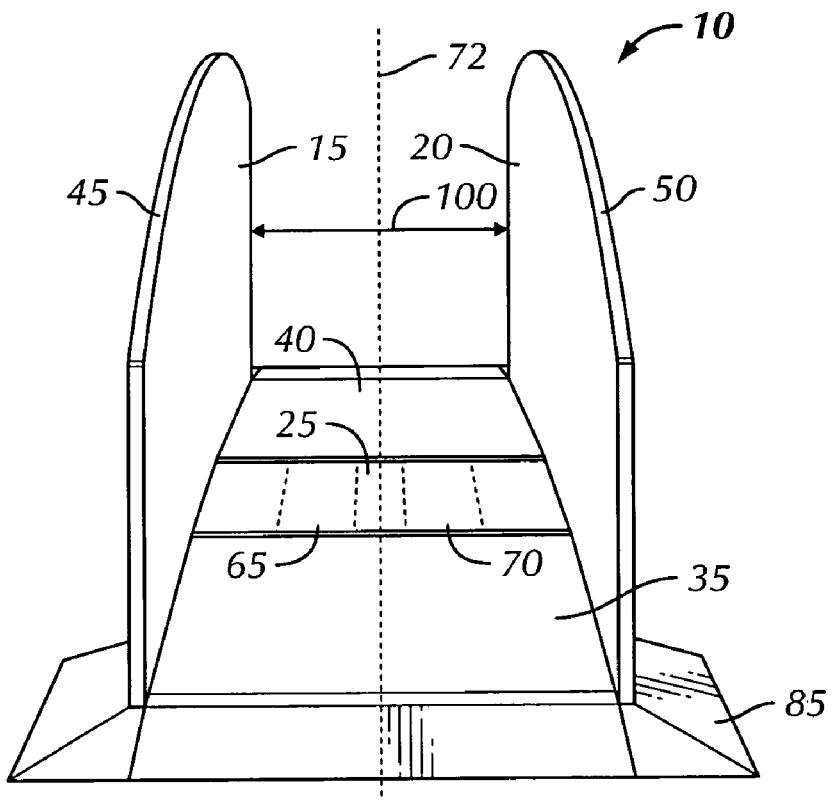

FIGS. 1, 2, and 3 are perspective, side, and end-views, respectively, of inspection system 10. The inspection system is shown embodied as a walkthrough shoe scanner and includes left wall 15 and right wall 20. Inductive sensor 25 is located between entrance ramp 35 and exit ramp 40. The left wall is supported by frame 45, and the right wall is supported by frame 50.

Figure 4:
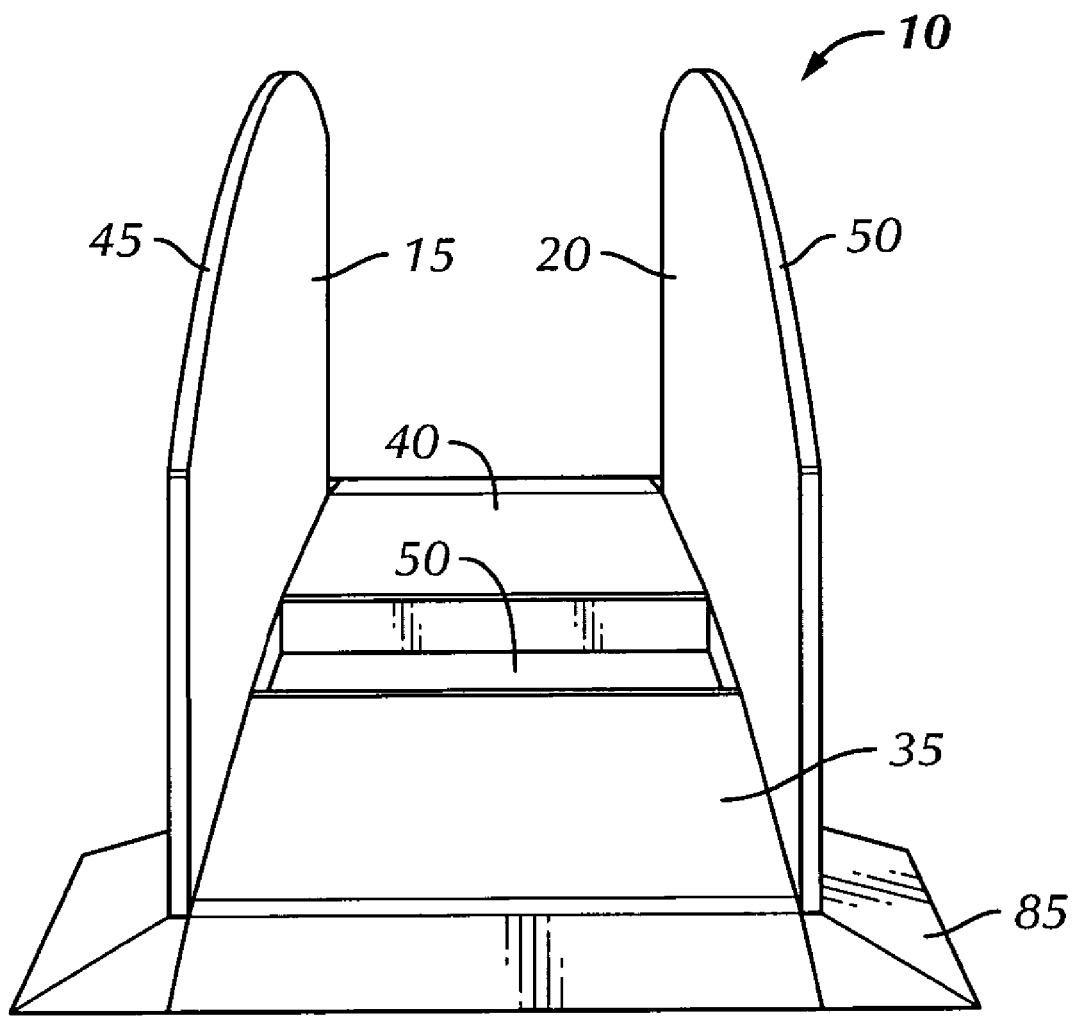
FIG. 4 is an end-view of the inspection system of FIGS. 1-3, the inductive sensor having been removed to show the sensor housing.

In accordance with an embodiment, the inductive sensor may be positioned within a recessed region of the walkway, between the entrance and exit ramps. This recessed region will also be referred to as the sensor housing. In FIG. 4, the inductive sensor has been omitted to show sensor housing 55, which is recessed within the walkway of inspection system 10.

As shown in FIGS. 1-3, inductive sensor 25 may be implemented using two anti-symmetric current branches 65 and 70. These current branches may be located on opposing sides of the medial plane of the inspection system. Specifically, as shown in FIG. 3, current branch 65 is positioned on one side of medial plane 72, while current branch 70 is positioned on the opposite side of the medial plane.

Inductive sensor 25 may be configured in such a manner that both current branches experience current flow that is generally or substantially parallel to the left and right walls. For example, the current branches may be placed in communication with an electrical source (not shown in this figure). During operation, current flows through current branch 65 in one direction, while current flows through current branch 70 in substantially the opposite direction. The term "anti-symmetric current flow" may be used to refer to the condition in which current flows through the current branches in substantially opposite directions.

Inductive sensor 25 may be implemented using a quadrupole resonance (QR) sensor, a nuclear magnetic resonance (NMR) sensor, a metal detection sensor, and the like. For convenience only, various embodiments will be described with reference to the inductive sensor implemented as a QR sensor, but such description is equally applicable to other types of inductive sensors.

Referring still to FIGS. 1-3, current branches 65 and 70 collectively define a QR sheet coil or a QR tube array coil. For convenience only, further discussion of the QR sensor will primarily reference a "QR sheet coil," or simply a "QR coil," but such description applies equally to a QR tube array coil. During a typical inspection process, a person enters the system at entrance 75, and then stands within an inspection region defined by QR sensor 25. Specifically, the person may stand with their left foot positioned relative to current branch 65 and their right foot positioned relative to current branch 70. The QR sensor then performs an inspection process using nuclear quadrupole resonance (NQR) to detect the presence of a target substance associated with the person.

An appropriately configured QR sensor can detect a wide range of explosives such as Semtex, C-4, nitroglycerin, PETN, RDX, Detasheet, TNT, Tetryl, ANFO, black powder, and the like. If desired, the QR sensor may be configured with additional screening capabilities for detecting conductive objects, controlled substances, or illegal drugs such as cocaine, heroin, and MDMA, among others.

NQR is a branch of radio frequency spectroscopy that has been used for the detection of explosives and drugs, for example. NQR exploits the inherent electrical properties of atomic nuclei. Nuclei with non-spherical electric charge distributions possess electric quadrupole moments. In solid materials, electrons and atomic nuclei produce electric field gradients. These electric field gradients interact with the nuclear quadrupole moments of quadrupolar nuclei, producing energy levels for the quadrupolar nuclei, and hence their characteristic transition frequencies. Measurements of these frequencies, or relaxation time constants, or both, can indicate not only which nuclei are present but also their chemical environment.

During the inspection process, using carefully tuned pulses, or sequences of pulses, of low intensity electromagnetic RF waves, a quadrupole resonance device probes the molecular structure of targeted items such as explosives and narcotics. The effects of quadruple resonance momentarily disturb the alignment of target nuclei within the item scanned. As the nuclei realign themselves after the RF energy is turned off, they emit a characteristic signal of their own, which is picked up by a receiver and sent to a computer for analysis. The signal emitted by each type of explosive or illegal drug is unique. Specialized RF pulse sequences have been developed for optimal detection of particular explosives and illegal drugs such as cocaine and heroin. RF signal production and the detection of NQR return signals may be accomplished using, for example, the techniques disclosed in U.S. Pat. Nos. 5,592,083 and 6,847,208, both of which are assigned to Quantum Magnetics, Inc., of San Diego, Calif.

In general, QR sensor 25 includes, or is in communication with, a RF subsystem which provides electrical excitation signals to current branches 65 and 70. Using well-known techniques, the RF subsystem may utilize a variable frequency RF source to provide RF excitation signals at a frequency generally corresponding to a predetermined, characteristic NQR frequency of a target substance. During the inspection process, the RF excitation signals generated by the RF source may be introduced to the specimen, which may include the shoes, socks, and clothing present on the lower extremities of a person standing or otherwise positioned relative to the QR sensor. In some embodiments, the QR coil may serve as a pickup coil for NQR signals generated by the specimen, thus providing an NQR output signal which may be sampled to determine the presence of a target substance, such as an explosive.

As with other types of inductive sensors, QR sensor 25 typically requires some degree of EMI/RFI (electromagnetic interference/radio frequency interference) shielding from external noise. In addition, the QR sensor may also need shielding which inhibits RFI from escaping from the inspection system during an inspection process. The best RFI shielding is normally an electrically connected and grounded box that completely encloses the RF coil of the QR sensor. This arrangement prevents external noise from directly reaching the RF coil. Another common shielding technique is to position the RF coil within an enclosure having a wave-guide tunnel extension. However, these solutions are not always practical for inspecting humans, for example, since some people are wary or uncomfortable about having to walk and stand in confined spaces.

In accordance with embodiments of the present invention, constructing the QR sensor so that it does not excite the poorly attenuated modes, but rather only excites the well-attenuated modes, may reduce the amount of shielding required by the QR sensor. The specifics regarding this aspect of the QR sensor are described in conjunction with FIGS. 5-10.

FIGS. 1-4 show one example of a passive, open-access RF shield which may be used in conjunction with a QR sensor. Shielding for the inspection system may be accomplished by electrically connecting left and right walls 15 and 20, entrance and exit ramps 35 and 40, and sensor housing 55. Each of the shielding components may be formed from a suitably conductive material such as aluminum or copper. Typically, the floor components (ramps 35 and 40, and sensor housing 55) are welded together to form a unitary structure. The left and right walls may also be welded to the floor components, or secured using suitable fasteners such as bolts, rivets, or pins. QR sensor 25 may be secured within sensor housing 55 using, for example, any of the just-mentioned fastening techniques. The left and right walls, entrance and exit ramps, and the sensor housing collectively define a substantially U-shaped shielded structure which provides a walkway through which persons may pass during an inspection process.

If desired, the left and right walls, the entrance and exit ramps, and the QR sensor may be covered with non-conducive materials such as wood, plastic, fabric, fiberglass, and the like. Inspection system 10 is shown having optional entrance and exit surrounds 85 and 90. These surrounds facilitate the ingress and egress of people walking through the inspection system.

Optimally, the overall size and shape of the inspection system is sufficient to provide the necessary electromagnetic shielding for the inductive sensor being implemented (for example, QR sensor 25). FIG. 2 shows left and right walls 15 and 20 having an overall height 95. This height is defined as the distance between a top surface of QR sensor 25 and the highest portion of the walls. Inspection system 10 has width 100, which is defined by the distance between walls 15 and 20. FIG. 3 shows inspection system 10 having medial plane 72, which is approximately parallel to the walls of the inspection system.

In accordance with one embodiment, a typical walk-through inspection system may include walls having a height of about 28-42 inches, and a width of about 24-36 inches. The embodiment of FIGS. 1-4 show the left and right walls formed with an approximate arcuate shape having a radius which approximates the height of the walls. Note that the walls have been optionally truncated at the entrance and exit. Truncating the walls facilitates the movement of people through the system, and further extends the notion of openness of the inspection system.

Figure 5A:
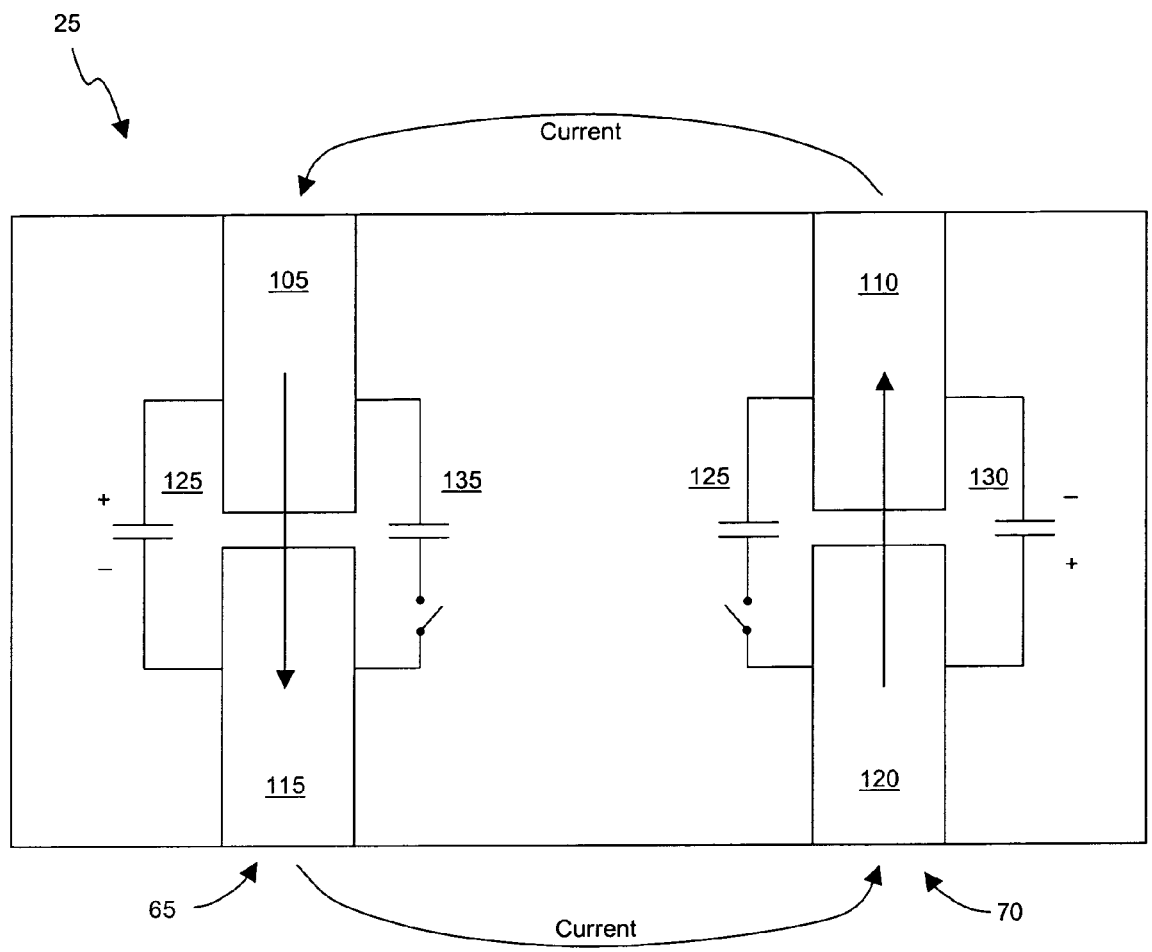
FIGS. 5A and 5B are schematic diagrams depicting primary electrical components of an inductive sensor.

FIG. 5A is a simplified schematic diagram depicting some of the primary electrical components of QR sensor 25. Left current branch 65 is shown having upper and lower conductive elements 105 and 115, which are separated by a non-conductive region. Similarly, right current branch 70 includes upper and lower conductive elements 110 and 120, which are also separated by a non-conductive region. The left and right current branches collectively define the QR coil of the sensor, were previously shown physically in FIGS. 1 and 3, and may be formed from any suitably conductive materials such as copper or aluminum, for example.

No particular length or width for the current branches is required. In general, each current branch may be dimensioned so that it is slightly larger than the object or specimen being inspected. Using a typical walkthrough inspection system as an example, a person's left foot and right foot (with or without shoes) may be respectively placed in close proximity to the left and right current branches. This may be accomplished by the person standing over the left and right current branches. In this scenario, the left and right branches may each have a width of about 4-8 inches and a length of about 12-24 inches. It is to be understood that the terms "left" and "right" are merely used for expositive convenience and are not definitive of particular sides of the structure.

Upper and lower conductive elements 105 and 115 are shown electrically coupled by fixed-valued resonance capacitor 125 and tuning capacitor 135, which is a switched capacitor that is used to vary tuning capacitance. Upper and lower conductive elements 110 and 120 may be similarly configured.

FIG. 5A also includes several arrows which show the direction of current flow through the left and right current branches. During operation, current flows through left current branch 65 in one direction, while current flows through right current branch 70 in substantially the opposite direction. The reason that current flows through the two current branches in opposite directions is because the left and right current branches have a different arrangement of positive and negative conductive elements. For instance, left current branch 65 includes a positive upper conductive element 105 and a negative lower conductive element 115. In contrast, right current branch 70 includes a negative upper conducive element 110 and a positive lower conductive element 120. This arrangement is one example of a QR sensor providing counter-directed or anti-symmetric current flow through the current branches.

In accordance with an embodiment, current flows between the left and right current branches during operation since these components are electrically coupled via ramps 35 and 40, and the sensor housing 55. During operation, a person may place their left foot over left current branch 65 and their right foot over right current branch 70. In such a scenario, current is directed oppositely through each branch resulting in current flowing from toe to heal along left current branch 65, and from heal to toe along right current branch 70.

Figure 5B:
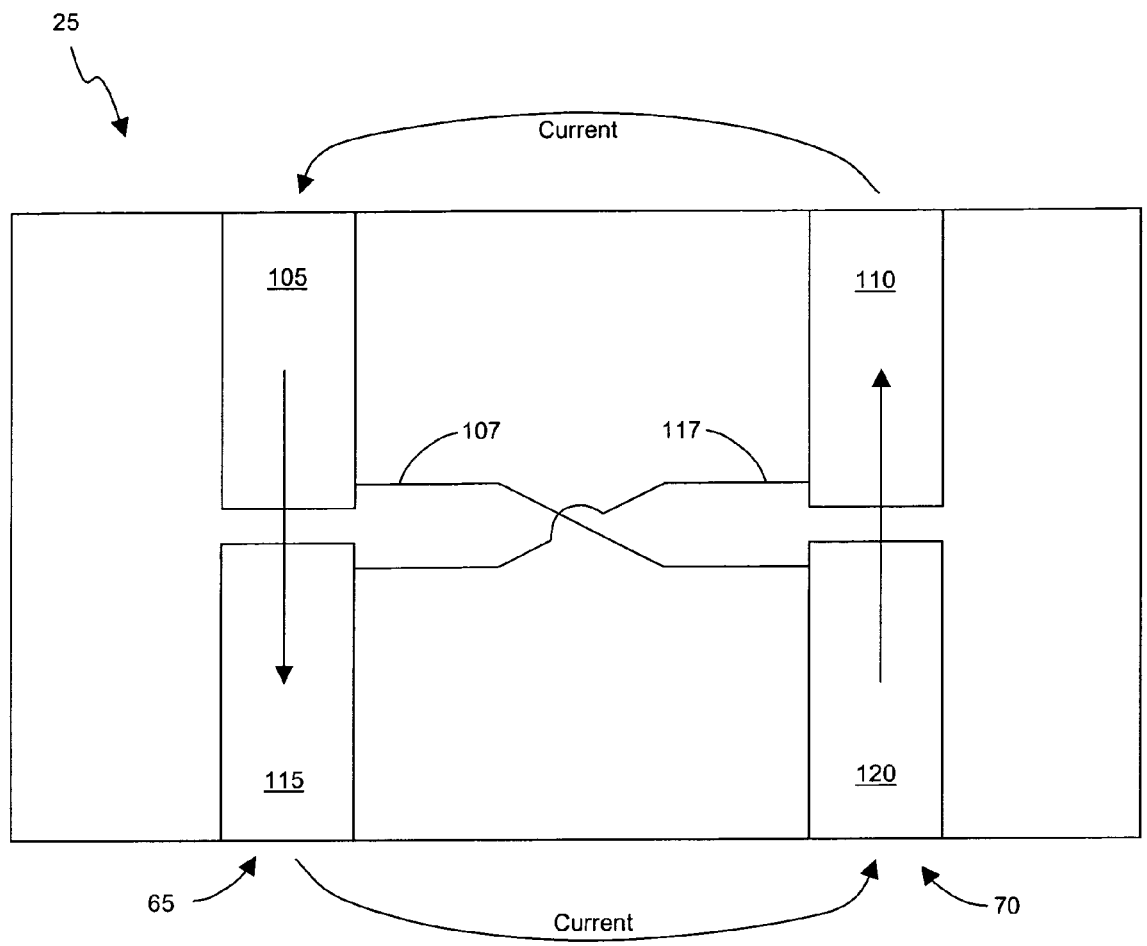

FIG. 5B is a simplified schematic diagram depicting optional current balance wires in communication with the left and right current branches of QR sensor 25. Note that FIG. 5B depicts the same QR sensor of FIG. 5A, but fixed-valued resonance capacitor 125 and tuning capacitor 135 of the left and right current branches have been omitted for clarity.

In FIG. 5B, current balance wire 107 is shown electrically coupling upper conductive element 105 and lower conductive element 120. Current balance wire 117 similarly couples lower conductive element 115 and upper conductive element 110. The balance wires assist the QR sensor in maintaining the above-described anti-symmetric flow of current through current branches 65 and 70. In addition, these current branches enable the positive and negative terminals of left and right current branches 65 and 70 to maintain the same, or substantially the same, current level.

Figure 6:
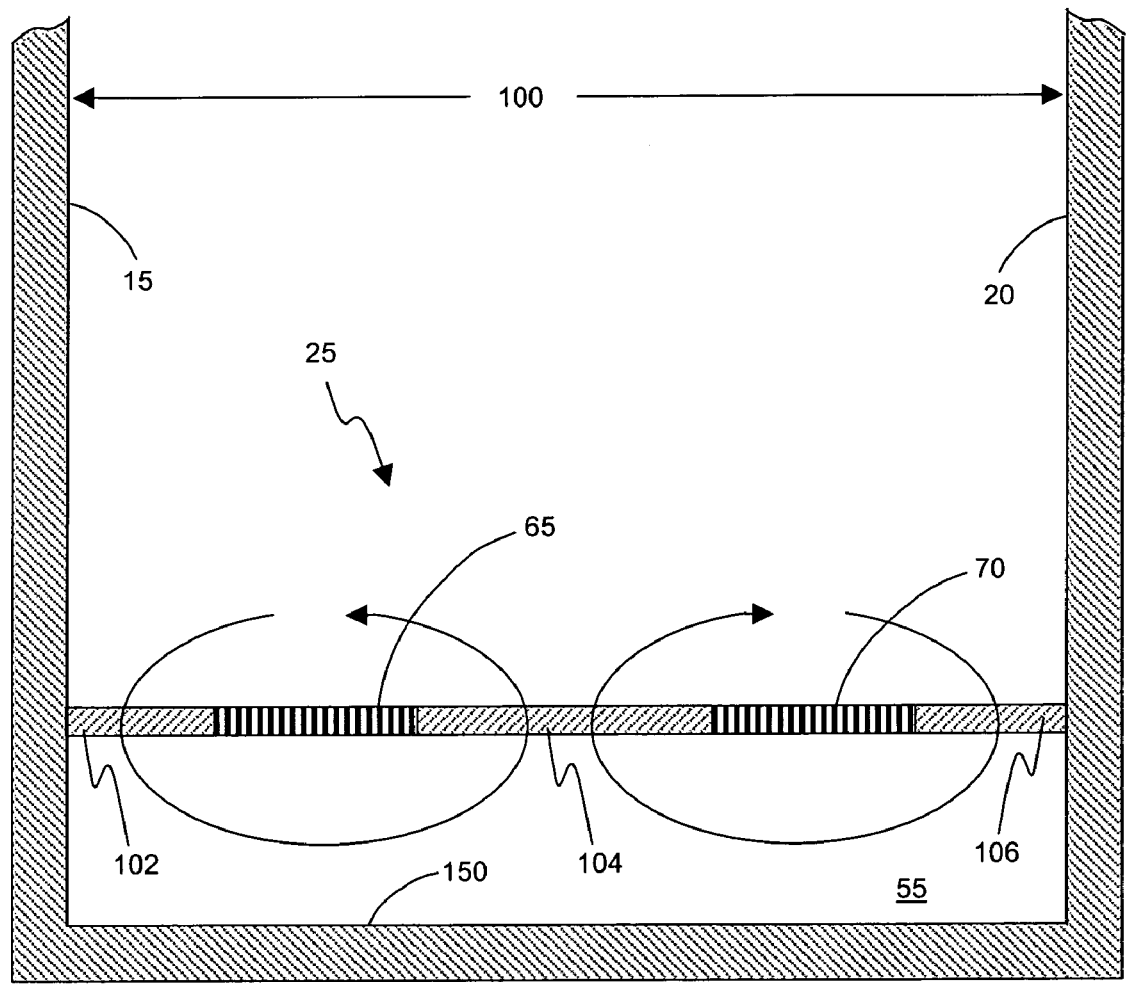
FIG. 6 is a partial cross-sectional view of the inspection system of FIGS. 1-3, showing the inductive sensor positioned within the sensor housing.

FIG. 6 is a partial cross-sectional view of QR inspection system 10, showing QR sensor 25 positioned within sensor housing 55. Left current branch 65 is shown producing a magnetic field which circulates in a counter-clockwise direction about the current branch. In contrast, right current branch 70 produces a magnetic field which circulates in a clockwise direction about the current branch. The direction of the magnetic fields generated by each current branch results from the particular direction of the current flowing through each respective branch. Since the current flows through each branch in opposite directions, as shown in FIGS. 5A and 5B, the magnetic fields generated by each of these branches likewise circulate in opposite directions. The QR sensor shown in FIG. 6 produces counter-directed magnetic fields which individually circulate about left or right current branches 65 and 70.

Note that the QR sensor is typically positioned within sensor housing 55 to form a non-conductive gap between current branches of the QR sensor and bottom 150 of the sensor housing. This gap allows the magnetic fields to circulate about their respective current branches. In a typical walkthrough inspection system, this gap would be, at a minimum, about 2-5 inches. There is no maximum dimension for this gap.

In contrast to conventional inductive sensor systems, the counter-directed magnetic fields generated by QR sensor 25 are well-attenuated and are especially suited for use with open-access shielding structures. For example, the resulting pattern of the magnetic fields generated by QR sensor 25 experiences an approximately exponential drop in strength along a radial direction given by $e^{-r/w}$, in which 'r' is the radius of the walls (distance 95 of FIG. 2) and 'w' is the lateral spacing between the walls (distance 100 of FIG. 3).

In the embodiment of FIG. 6, the QR sensor is implemented using a printed circuit board (PCB). The left and right current branches are electrically isolated from each other, and from conductive walls 15 and 20, by non-conductive regions 102, 104, and 106. These non-conductive regions permit the magnetic fields to circulate about their respective current branches. As an example of a practical application, the left and right current branches may be positioned about 2-7 inches from their respective walls using non-conductive regions 102 and 106. In addition, the current branches may be positioned about 4-14 inches from each other using non-conductive region 104.

Current branches 65 and 70 are shown having approximately the same thickness as the PCB, but this is not a requirement and in many situations these components are much thinner. In a typical walkthrough inspection system, for example, the conductive current branches do not require any particular thickness. However, typical current branches may have a thickness which is on the order of about $1/16$-$5/8$ of an inch.

Operation of a walkthrough QR inspection system in accordance with embodiments of the invention may proceed as follows. First, a person may be directed to enter QR inspection system 10 at entrance 75. The person proceeds up entrance ramp 35 and stands with their feet positioned over QR sensor 25. To maximize the accuracy of the inspection process, the person will stand with their left foot positioned over left current branch 65 and their right foot over right current branch 70.

At this point, the lower extremities of the person are QR scanned by QR sensor 25 to determine the presence of a target substance such as, for example, an explosive, contraband, an illegal drug, a controlled substance, or a conductive object. This may be accomplished by the QR sensor providing RF excitation signals at a frequency generally corresponding to a predetermined, characteristic NQR frequency of the target substance. For example, RDX-based plastic explosives have a resonant frequency of approximately 3.410 MHz, while PETN-based plastic explosives have a resonant frequency of approximately 890 KHz. Note that the excitation frequency need not be exactly the same as the target substance NQR frequency, but it is typically within about 500-1000 Hz. The resonant frequencies of the various target substances that may be detected using NQR are well known and need not be further described.

When acting as a pickup coil, QR sensor 25 may then detect any NQR signals from the target specimen. These signals may be communicated to a suitable computing device for processing and analysis, as will be described in more detail below. A typical QR scanning process requires about 2-20 seconds. This inspection process provides for quick, accurate, non-intrusive inspection of the lower extremities of an inspected person. Explosives, contraband, and other items of interest located in proximity to a person's footwear, socks, trousers, and other clothing items present at the lower extremities may be detected. Note that footwear, socks, and other clothing items need not be removed prior to inspection. These items can be inspected by the QR inspection system while being worn by the inspected person. Since the inspected person is not required to remove such items before inspection, the QR inspection system is especially suited for the non-intrusive inspection of passengers as part of a multi-station, airport screening checkpoint.

In some embodiments, QR inspection system 10 may utilize QR sensor 25 to additionally or alternatively detect metallic objects, such as guns, ice picks, knives, razors, and other bladed weapons, present near the lower extremities of the inspected person. A person's shoe is a common location for concealing knives and other bladed weapons. In one implementation, QR sensor 25 may be designed to detect a change or shift in the QR tune frequency resulting from the presence of a conductive object located in proximity to the lower extremities of the inspected person. This shift in QR tune frequency may be correlated to the presence of a weapon, such as a knife, concealed within the inspected person's shoe. The QR sensor is useful for detecting conductive objects positioned in a number of different orientations relative to the current branches of the QR sensor, and thus may be used to detect concealed weapons as part of the inspection process.

Figure 7A:
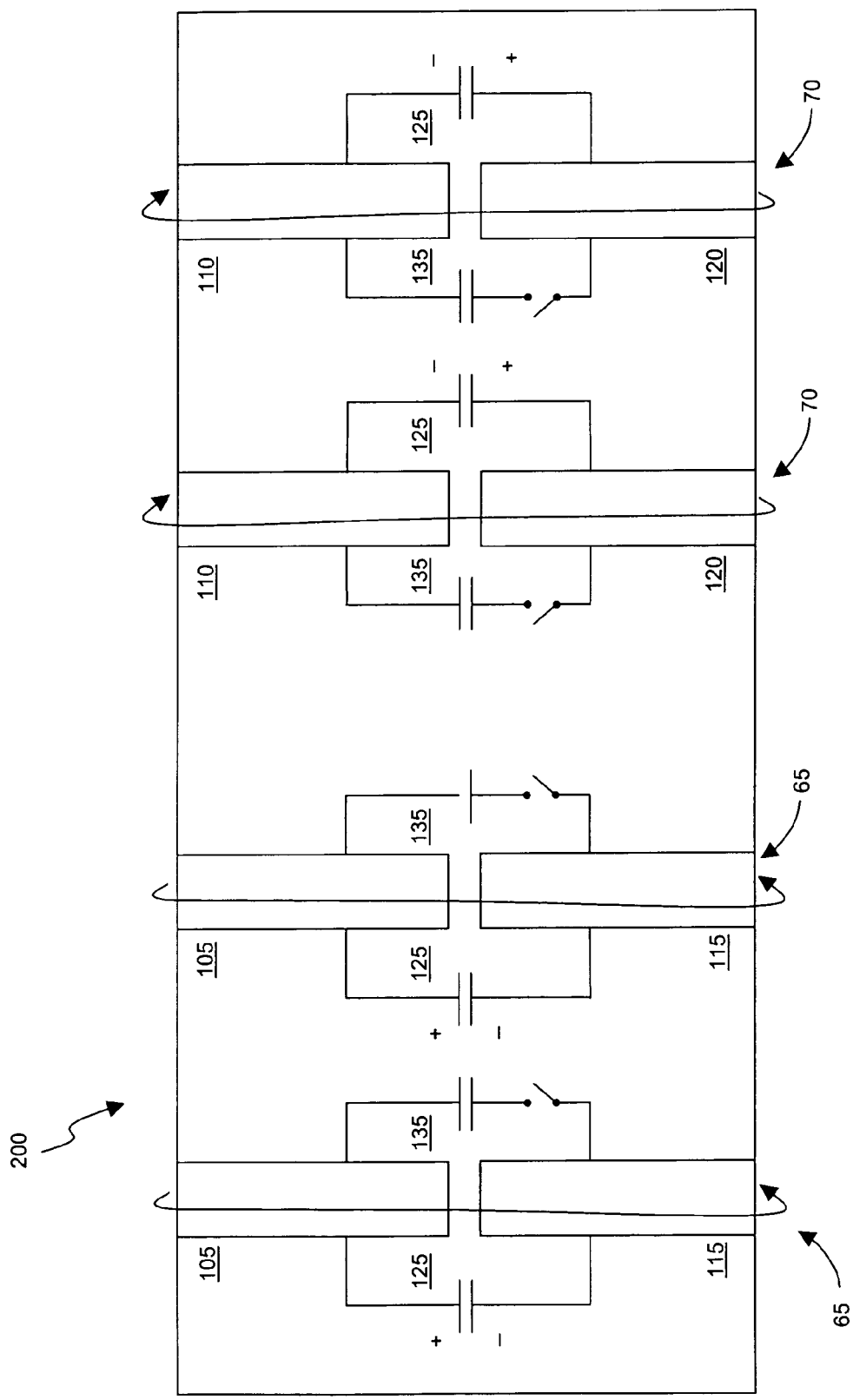
FIGS. 7A and 7B are schematic diagrams depicting primary electrical components of an inductive sensor in accordance with an alternative embodiment of the present invention.

FIG. 7A is a simplified schematic diagram depicting some of the primary electrical components of QR sensor 200, in accordance with an alternative embodiment of the present invention. Similar to other embodiments, QR sensor 200 may be sized to be received within sensor housing 55 of the inspection system. As such, two current branches 65 may be positioned on one side of medial plane 72 of the inspection system (FIG. 3), and two current branches 70 may be positioned on the opposing side of the medial plane. For ease of discussion, the two sides of the medial plane will sometimes be referred to as the left and right sides. Both current branches 65 are shown having upper and lower conductive elements 105 and 115, and both current branches 70 have upper and lower conductive elements 110 and 120.

FIG. 7A also includes several arrows which show the direction of current flow through the various current branches of the QR sensor. During operation, current flows through the left-two current branches 65 in one direction, while current flows through the right-two current branches 70 in substantially the opposite direction. Once again, the reason that current flows through the current branches in opposite directions is because the left-two and the right-two current branches have a different arrangement of positive and negative conductive elements.

In accordance with an embodiment, the illustrated current flow may be accomplished by electrically coupling these current branches to ramps 35 and 40, and sensor housing 55. During operation, a person may place their left foot over the two left current branches 65 and their right foot over the two right current branches 70.

Figure 7B:
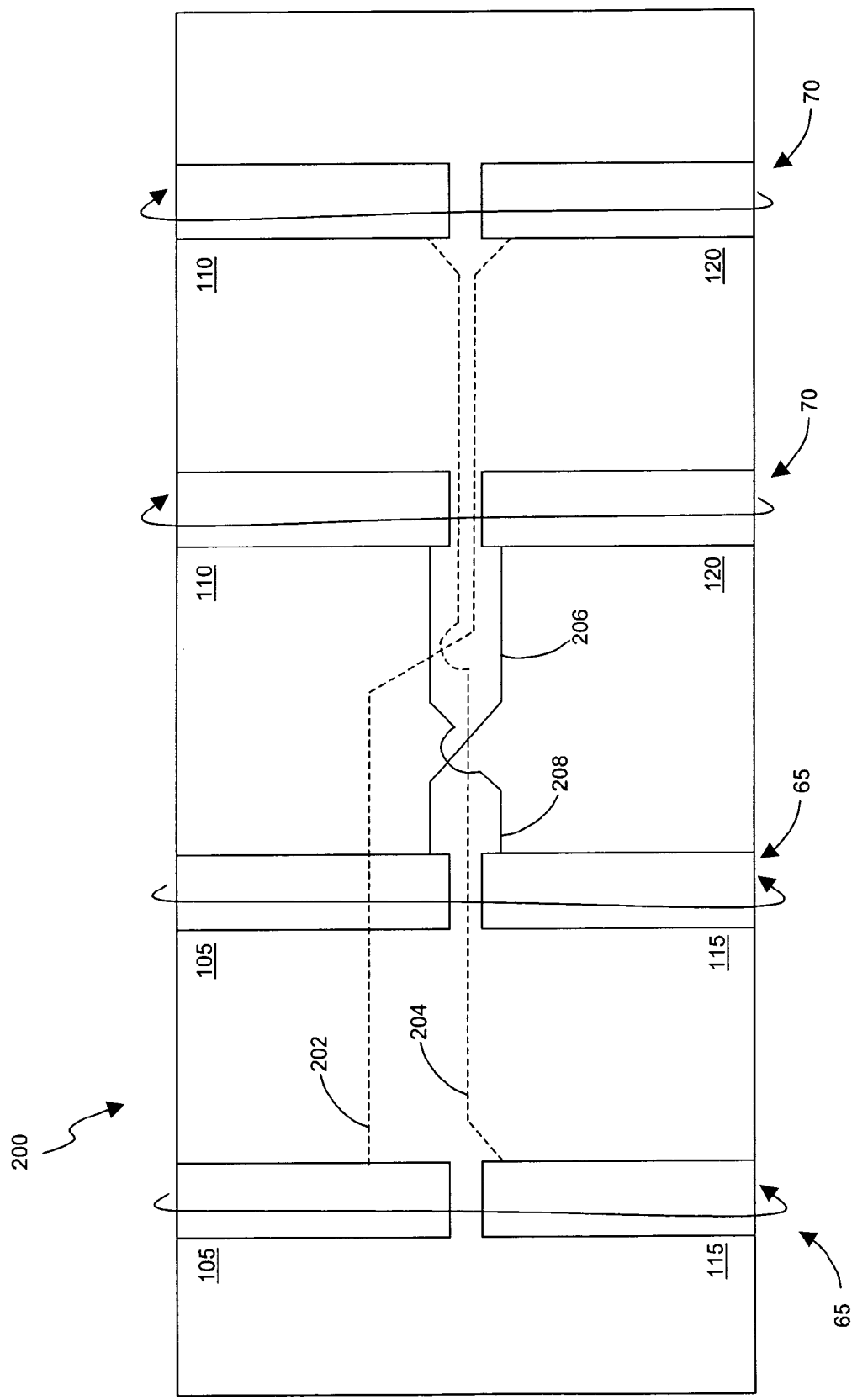

FIG. 7B is a simplified schematic diagram depicting optional current balance wires in communication with the various current branches of QR sensor 200. Note that FIG. 7B depicts the same QR sensor of FIG. 7A, but fixed-valued resonance capacitor 125 and tuning capacitor 135 of the various current branches have been omitted for clarity.

In FIG. 7B, current balance wire 202 is shown electrically coupling upper conductive element 105 of the outer current branch 65 with lower conductive element 120 of the outer current branch 70. Current balance wire 204 similarly couples lower conductive element 115 of the outer current branch 65 with upper conductive element 110 of the outer current branch 70. Current balance wire 206 electrically couples upper conductive element 105 of the inner current branch 65 with lower conductive element 120 of the inner current branch 70. Current balance wire 208 similarly couples lower conductive element 115 of the inner current branch 65 with upper conductive element 110 of the inner current branch 70

The balance wires assist the QR sensor in maintaining the anti-symmetric flow of current between the right-two current branches 65 and the right-two current branches 70. In addition, these current branches enable the connected conductive elements to maintain the same, or substantially the same, current level.

Figure 8:
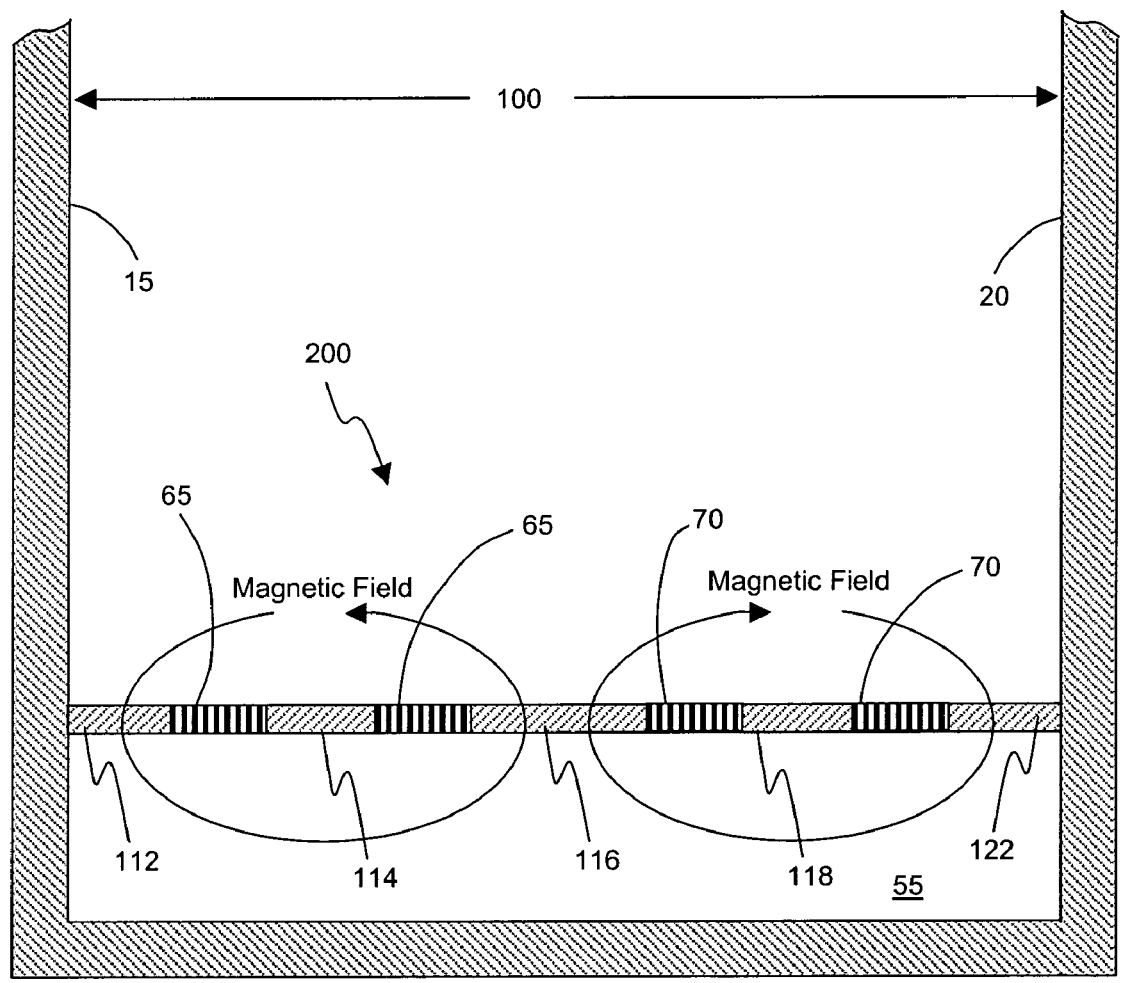
FIG. 8 is a partial cross-sectional view of the inspection system of FIGS. 1-3 implementing an inductive sensor in accordance with FIGS. 7A and 7B.

FIG. 8 is a partial cross-sectional view of QR inspection system 10, showing QR sensor 200 positioned within sensor housing 55. The left-two current branches 65 are shown collectively producing a magnetic field which circulates in a counter-clockwise direction about these two current branches. In contrast, the right-two current branches 70 collectively produce a magnetic field which circulates in a clockwise direction about these two current branches.

The direction of the magnetic fields generated by these current branches results from the particular direction of the current flowing through each respective current branch. Since current flows through each of the left-two current branches 65 in substantially the same direction (FIG. 7B), these two current branches cooperate with each other to generate a single magnetic field which circulates about both of the current branches. For similar reasons, the right-two current branches 70 cooperate to generate a single magnetic field which circulates about both of these current branches. Accordingly, the QR sensor shown in FIG. 8 produces counter-directed magnetic fields using a plurality of adjacent current branches having current flow in one direction, and a plurality of adjacent current branches having current flow in substantially the opposite direction.

FIG. 8 shows QR sensor 200 utilizing two adjacent current carrying branches to produce magnetic fields in one of the two illustrated directions. If desired, the QR sensor may alternatively implement three or more adjacent current carrying branches to produce a magnetic field in a particular direction.

In the embodiment of FIG. 8, the various current branches are electrically isolated by non-conductive regions 112, 114, 116, 118, and 122. Operation of a walkthrough QR inspection system in accordance with the embodiment of FIG. 8 may proceed as follows. First, a person may be directed to enter QR inspection system 10 at entrance 75. The person proceeds up entrance ramp 35 and stands within the inspection region defined by QR sensor 200. Optimally, the person will stand with their left foot positioned over the left-two current branches 65 and their right foot over the right-two current branches 70. At this point, the lower extremities of the person may be QR scanned by QR sensor 25 to determine the presence of a target substance using any of the techniques previously described.

As before, no particular length or width for the current branches is required. In general, the overall size of the left-two current branches 65, and the included non-conductive region 114, may be dimensioned so that these components collectively define an area which is slightly larger than the object or specimen being inspected. The right-two current branches 70, and included non-conductive region 118, may be similarly dimensioned.

If desired, QR sensor 200 may also be used for detecting conductive objects present in the vicinity of the lower extremities of the inspected person. In some situations, the multiple current branch arrangement of QR sensor 200 provides a heightened degree of sensitivity for conductive objects, permitting the detection of conductive objects in a greater number of different orientations relative to the current branches of the QR sensor, as compared to an arrangement of a single pair of current branches.

Figure 9A:
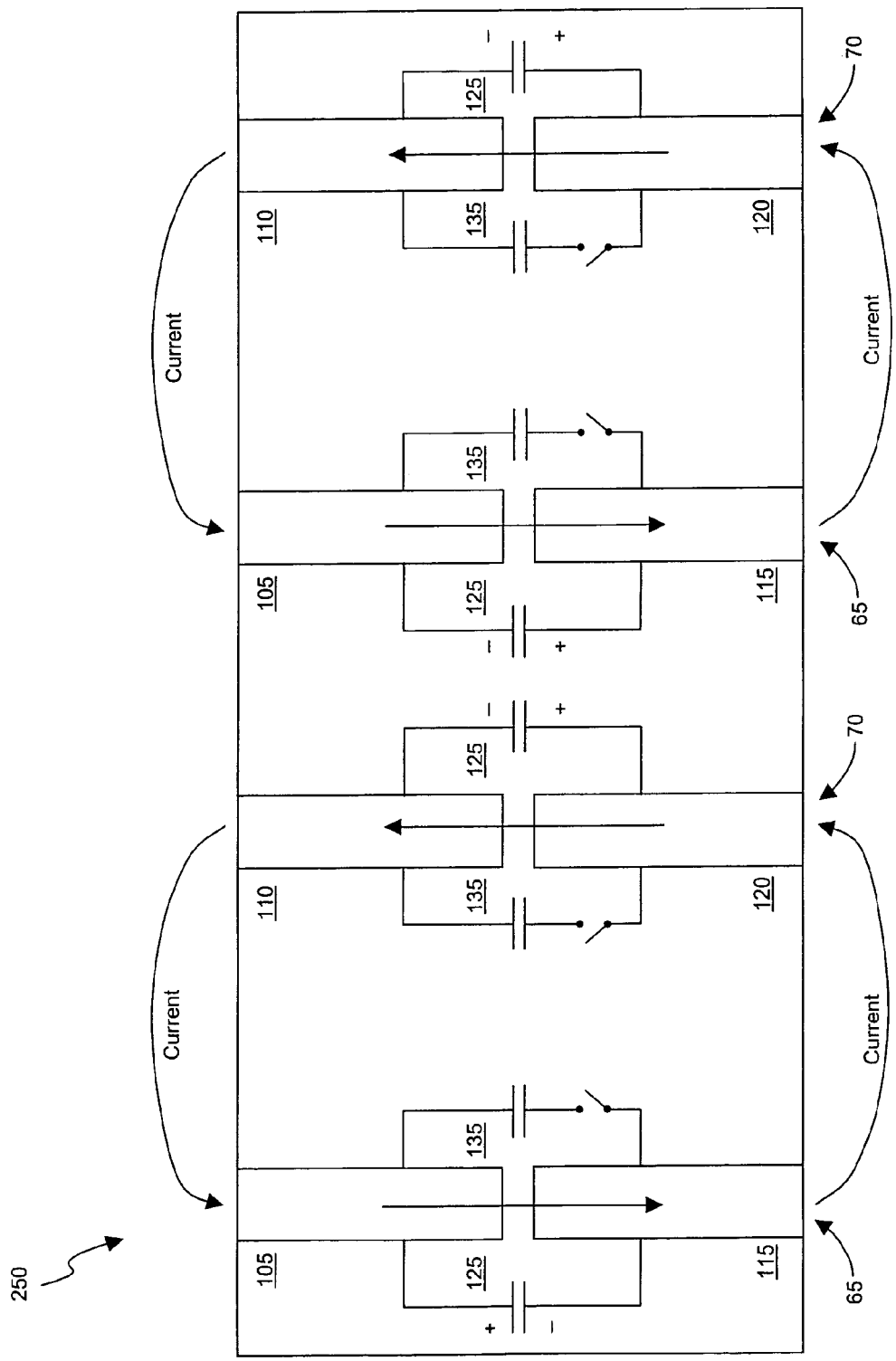
FIGS. 9A and 9B are schematic diagrams depicting primary electrical components of an inductive sensor in accordance with another alternative embodiment of the present invention.

FIG. 9A is a simplified schematic diagram depicting some of the primary electrical components of QR sensor 250, in accordance with an alternative embodiment of the present invention. QR sensor 250 is similar in many respects to QR sensor 200 of FIG. 7A. The primary distinction relates to the arrangement of the four current branches of the sensor. QR sensor 200 has two adjacent current branches 65 positioned on the left side of the sensor, and two adjacent current branches 70 positioned at the right side of the sensor. In contrast, QR sensor 250 utilizes adjacent current branches which have current flow in alternating directions. For example, looking from left to right, QR sensor 250 includes the following series of current branches: current branches 65, 70, 65, and 70. Current flows through each current branch 65 in one direction, and through each current branch 70 in another direction.

In accordance with an embodiment, the illustrated current flow may be accomplished by electrically coupling these current branches to ramps 35 and 40, and the sensor housing 55. Note that the inner two current branches 70 and 65 maybe positioned at such a distance from each other so that current does not flow between these branches.

Figure 9B:
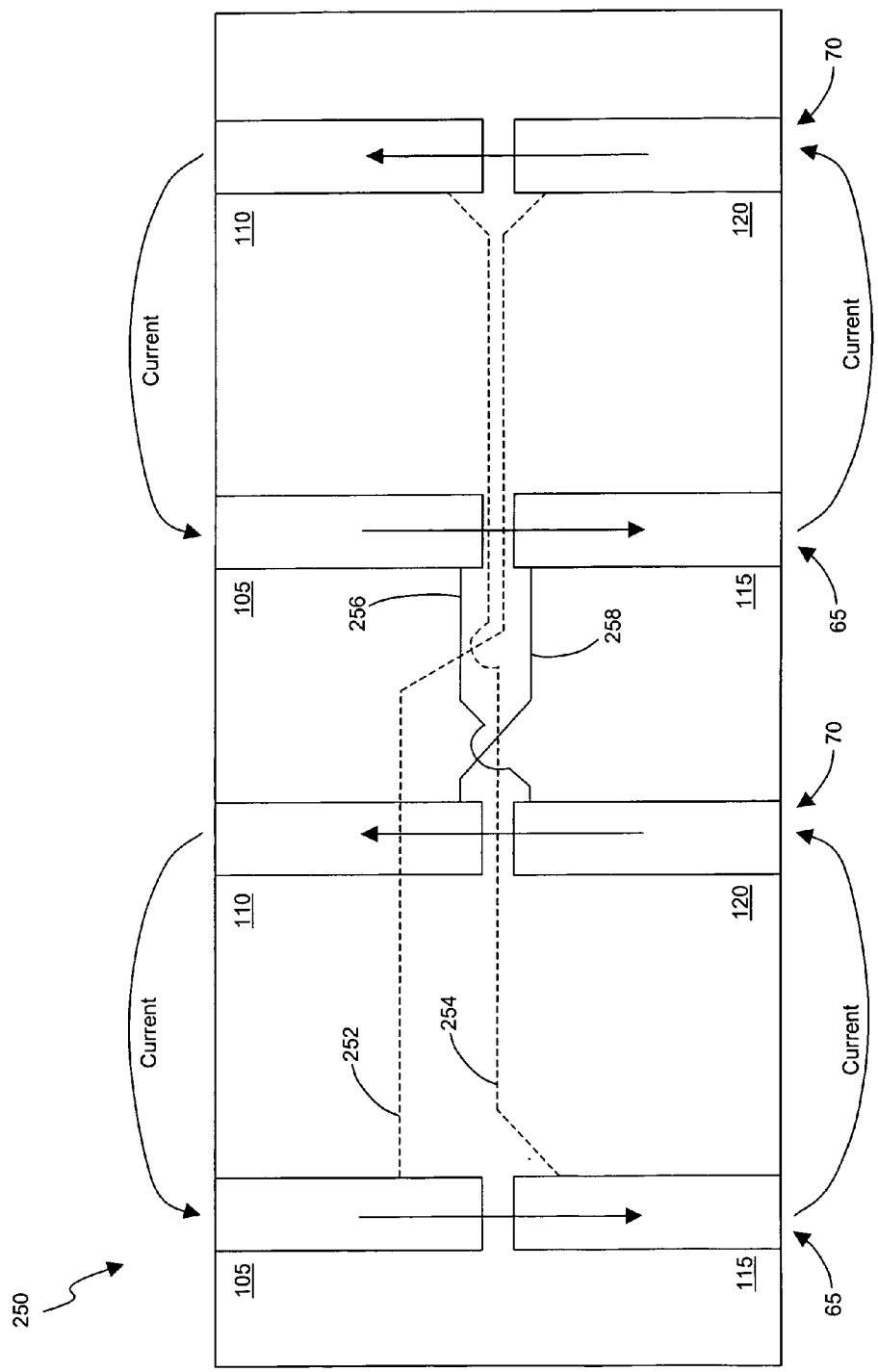

FIG. 9B is a simplified schematic diagram depicting optional current balance wires in communication with the various current branches of QR sensor 250. FIG. 9B depicts the same QR sensor of FIG. 9A, but fixed-valued resonance capacitor 125 and tuning capacitor 135 of the various current branches have been omitted for clarity. Similar to other embodiments, balance wires 252, 254, 256, and 258 electrically couple their respective conductive elements.

Figure 10:
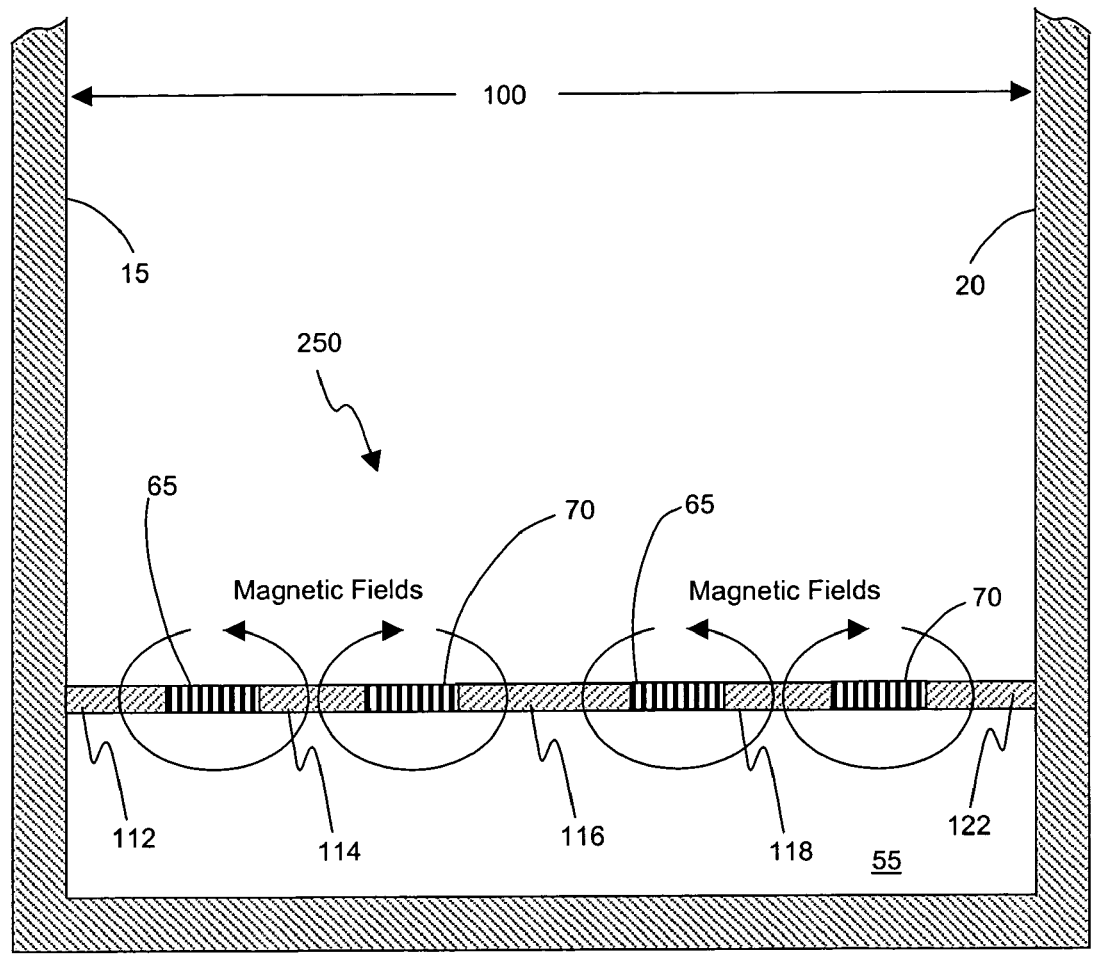
FIG. 10 is a partial cross-sectional view of the inspection system of FIGS. 1-3 implementing an inductive sensor in accordance with FIGS. 9A and 9B.

FIG. 10 is a partial cross-sectional view of QR inspection system 10, showing QR sensor 250 positioned within sensor housing 55. On the left side of the QR inspection system, current branch 65 produces a magnetic field which circulates in a counter-clockwise direction, and adjacent current branch 70 produces a magnetic field which circulates in a clockwise direction. The two current branches on the right side of the QR inspection system may be similarly configured to produce magnetic fields. If desired the embodiment of FIG. 10 may be modified to include additional pairs of current carrying branches. The embodiment of FIG. 10 is an example of a QR sensor having a plurality of current branches having current flow in one direction, and a plurality of current branches having current flow in substantially the opposite direction.

Operation of QR sensor 250 may proceed in manner similar to that described in other embodiments. Note that the alternating current branch arrangement of QR sensor 250 provides a certain degree of sensitivity for conductive objects, permitting the detection of such objects in orientations which may not be possible by the QR sensors of other embodiments. As such, the QR sensor arrangement of FIG. 10 may be used to augment or replace other types of QR sensors disclosed herein.

Figure 11:
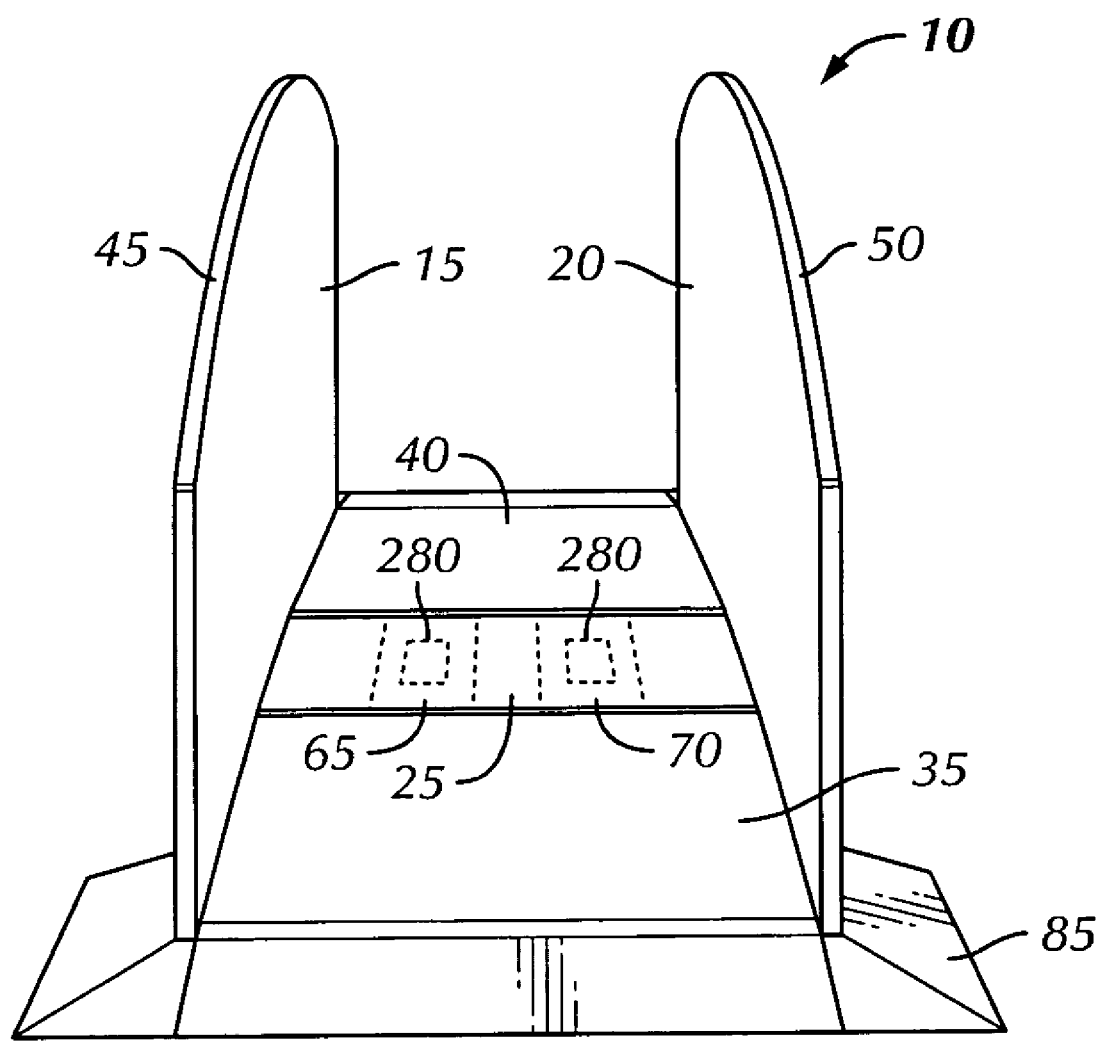
FIG. 11 is an end-view of the inspection system of FIGS. 1-3, the system further including an optional metal detector.

As described above, the QR sensor may be configured to detect metallic objects in a number of different orientations. To enhance the metal detection capability of inspection system 10, the inspection system may alternatively or additionally include a separate metal detection sensor. One example of such a system is shown in FIG. 11. In this figure, inspection system 10 is shown having metal detection sensors 280 in association with QR sensor 25. Each of the metal detection sensors maybe configured to detect conductive objects present within the vicinity of the lower extremities of the inspected person. Any variety of known metal detection sensors may be used, the specifics of which are not essential to the present invention.

A number of QR sensor embodiments, as well as different inspection systems, have been shown and described. It is again noted that various embodiments have been described with reference to a QR sensor, but such description applies equally to other types of inductive sensors such as NMR sensors and metal detection sensors. It will also be appreciated that still further alternative embodiments of the invention are possible. For example, the general structure of walls 15 and 20 are shown having a generally arcuate shape and truncated ends. If desired, these walls may alternatively be formed using rectangular, triangular, or other shapes. In addition, the walls are shown extending from the entrance and exit ramps at substantially right angles, but this is not critical and walls that extend at an acute or obtuse angle relative to the ramps are also possible.

Inspection system 10 is shown having an open-access entrance and exit, which is defined by the substantially U-shaped design of this structure. If desired, the inspection system may alternatively be configured with gates, doors, or other enclosure devices. Although the inspection system is fully functional without being enclosed within a shielded enclosure, such a design is possible. Note further that QR sensors in accordance with various embodiments of the present invention not only provide explosives screening, for example, as part of a walkthrough inspection system, but these QR sensors may be implemented to cooperate with other types of inspection systems as well (for example, metal detection, vapor trace, and the like). Examples of such embodiments will be described in conjunction with later figures.

Entrance and exit ramps 35 and 40 are shown as inclined ramps leading to the inductive sensor, but these components may be alternatively implemented as declining ramps, substantially horizontal structures, steps, and the like. Examples of such embodiments will be discussed in more detail with reference to later figures. The entrance ramp may be the same length and type as the exit ramp, or these components can be different.

QR sensor 25 has been shown positioned within recessed sensor housing 55. One alternative is to mount the sensor housing and included QR sensor onto a substantially flat portion of the walkway between the entrance and exit ramps. Such a configuration would require an inspected person to step up and onto the sensor housing for inspection.

The various inductive sensors disclosed herein may also be configured to cooperate with other types of inspection and detection systems. For example, a QR inspection system may be integrated with a walkthrough detection portal equipped with a sensor for scanning substantially an entire person, not just their lower or upper extremities, for explosives, weapons, or other contraband. One example of such as system is depicted in FIGS. 12-15.

Figure 12:
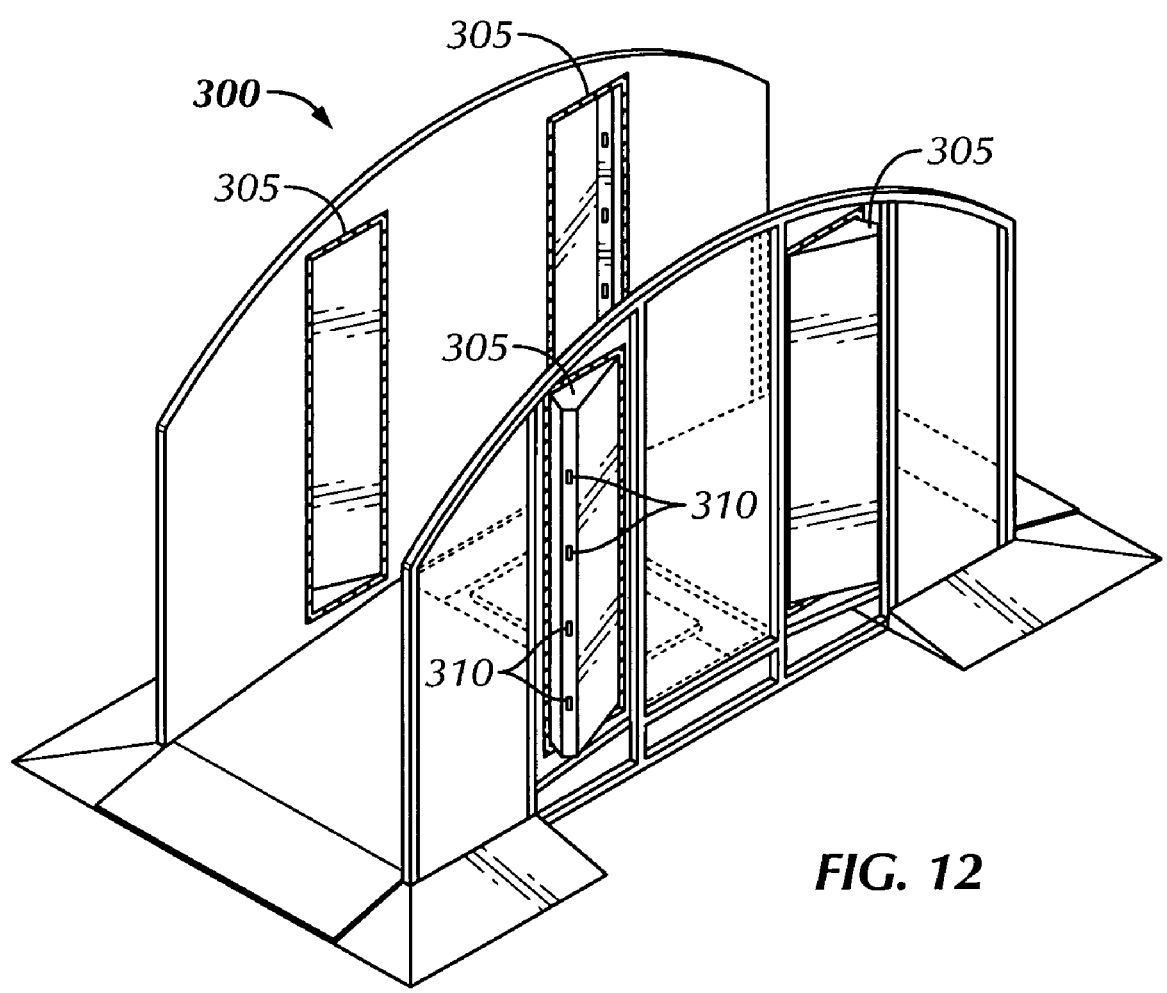
FIG. 12 is a perspective view of an inspection system which is adapted for use in a multi-sensor inspection system, in accordance with an alternative embodiment of the present invention.

FIG. 12 is a perspective view of QR inspection system 300, which contains a QR sensor 25 (not shown in this figure). System 300 is similar in many respects to QR inspection system 10, which is shown in FIG. 1. One distinction is that system 300 has been adapted to operate in conjunction with a portal detection system. In particular, system 300 includes four nozzle interfaces 305 which are individually formed within the walls of the QR inspection system. Each interface includes four nozzle apertures 310, which are sized to receive a linear jet array (not shown in this figure). Typically, the nozzle interfaces are welded, bolted, or otherwise attached or formed within their respective walls and may be constructed using the same conductive materials as the walls.

Figure 13:
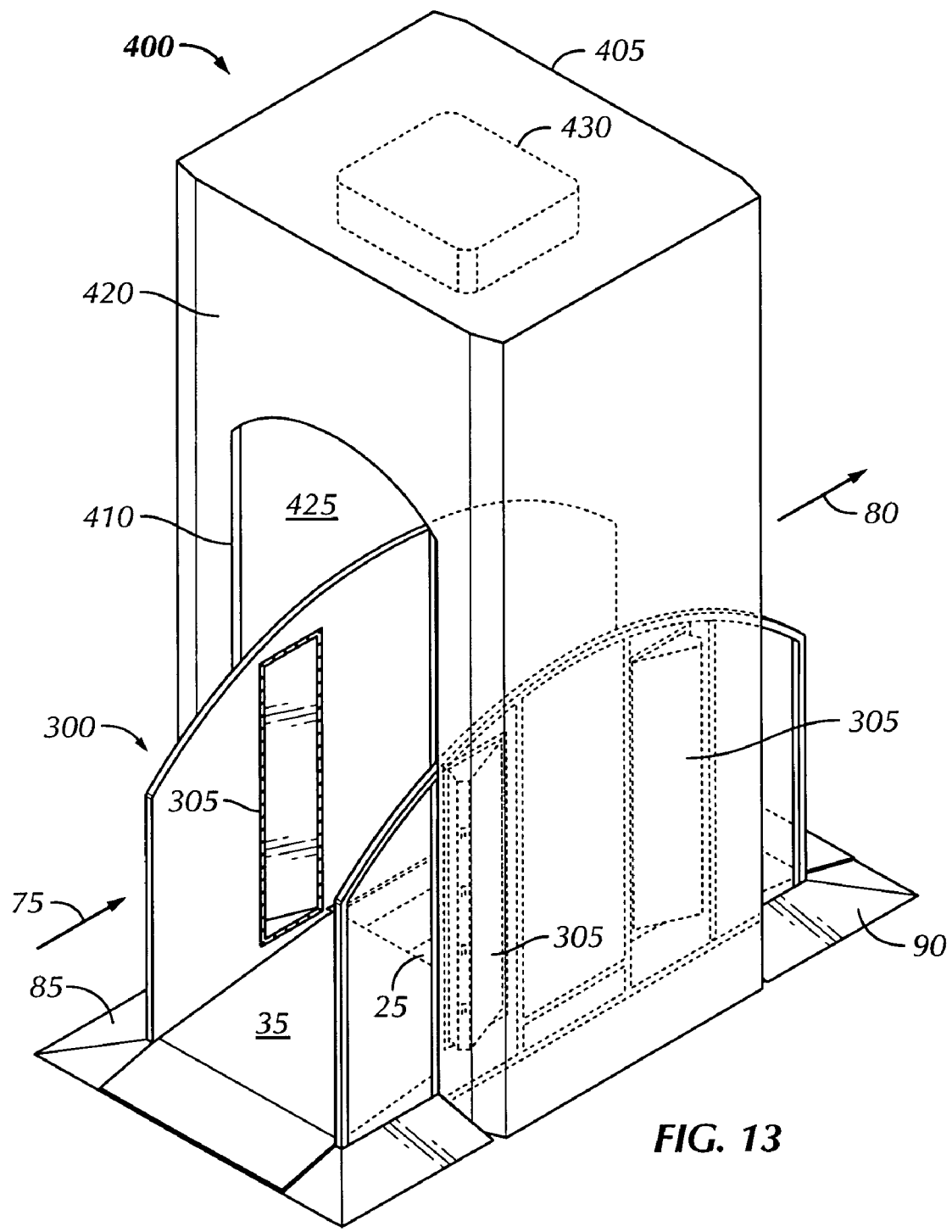
FIGS. 13 and 14 are perspective and end-views, respectively, of a multi-sensor inspection system in accordance with an embodiment of the invention.
Figure 14:
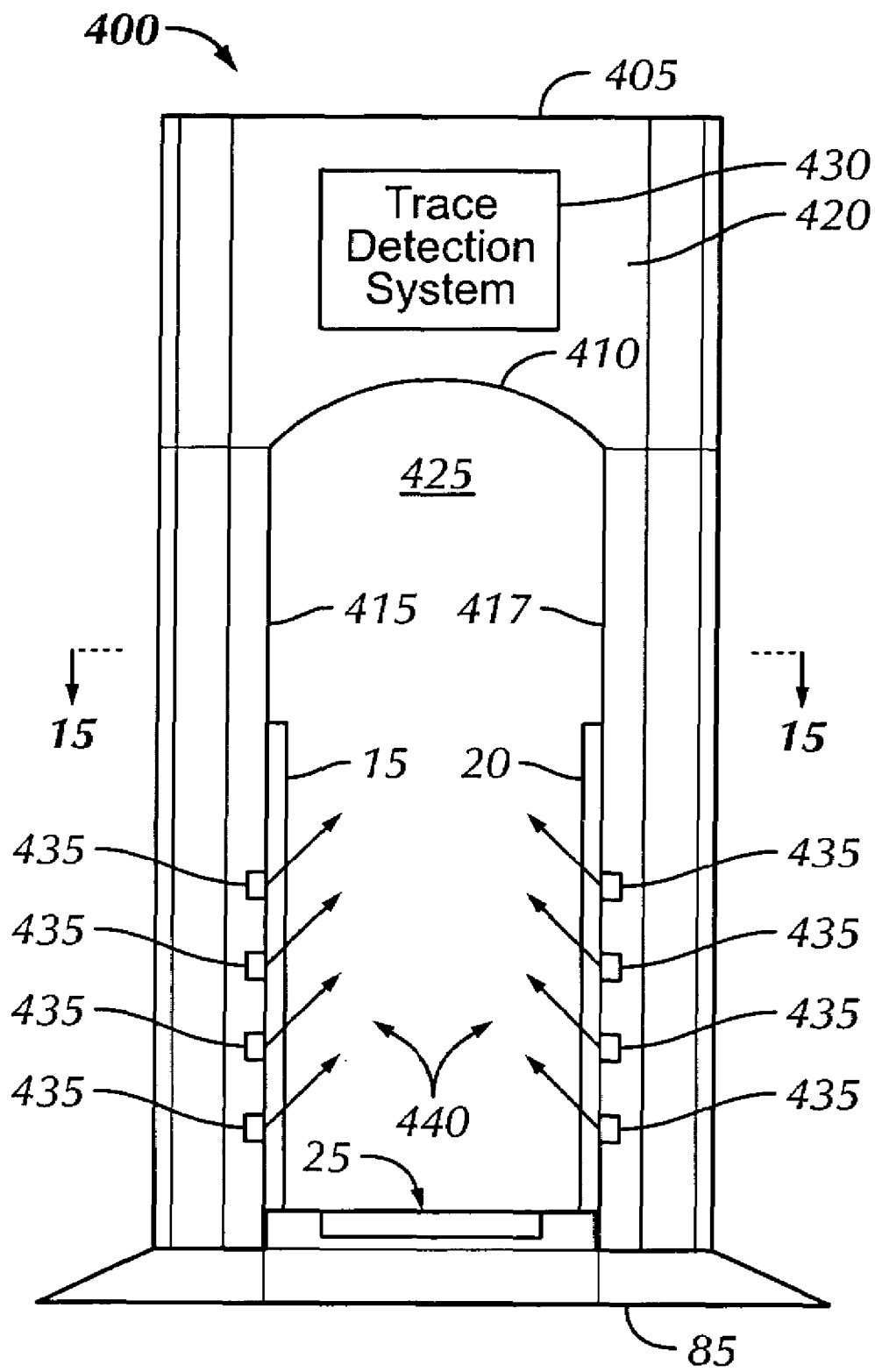
Figure 15:
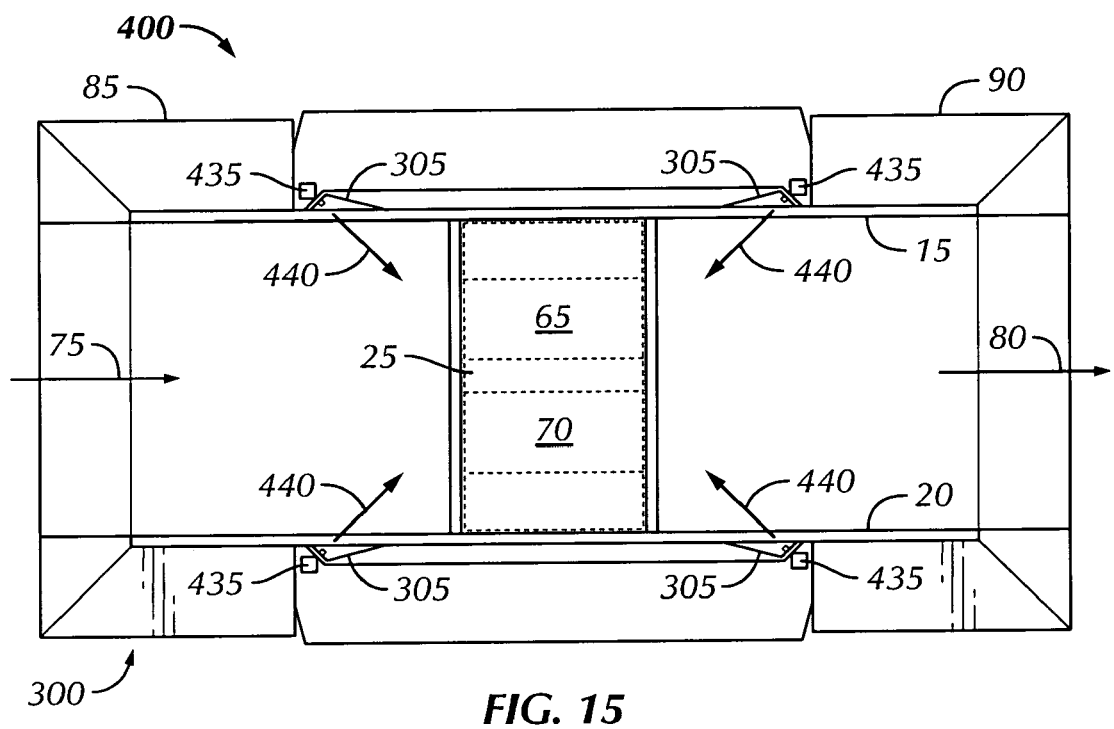
FIG. 15 is a cross-sectional view of a multi-sensor inspection system taken along line 15-15 in FIG. 14.

FIGS. 13 and 14 are perspective and end-views, respectively, of multi-sensor inspection system 400. FIG. 15 is a cross-sectional view of the multi-sensor inspection system taken along line 15 of FIG. 14. The multi-sensor inspection system includes walkthrough QR inspection system 300 configured in association with portal detection system 405.

Portal detection system 405 includes portal 410 having sidewalls 415 and 417, a plastic ceiling or hood 420, and passage 425 extending between the sidewalls and beneath the ceiling. The ceiling may include an inlet with a fan for producing air flow that substantially matches the air flow rate provided by the human thermal plume. During operation, particles of interest will be entrained in the human thermal plume that exists in the boundary layer of air adjacent the inspected person, and will flow upwardly from the person to the detection apparatus in the ceiling of the portal. The ceiling further includes trace detection system 430, which is a system capable of detecting minute particles of interest such as traces of narcotics, explosives, and other contraband. System 430 may be implemented using, for example, an ion trap mobility spectrometer.

If desired, portal detection system 405 may further include a plurality of air jets 435. The jets are arranged to define four linear jet arrays 440 (FIG. 15) with the jets in each array being vertically aligned. The jets may be disposed in portal 410 to extend from a lower location approximately at knee level (for example, about 1-2 feet from the ground) to an upper location approximately at chest level (for example, about 4-5 feet from the ground). Each jet may be configured to direct a short puff of air inwardly and upwardly into passage 425 of the portal.

More particularly, as shown most clearly in FIG. 14, jets 435 may be aligned at an acute angle of approximately 30°-60° to the vertical. The jets communicate with a supply of high-pressure air in the range of 40-100 psi. The jets may include solenoid valves that communicate with and are controlled by a controller (not shown in this figure) to operate sequentially. The jets function to disturb the clothing of the human subject in the passage sufficiently to dislodge particles of interest that may be trapped in the clothing of the inspected person. However, the short puffs of air are controlled to achieve minimum disruption and minimum dilution of the human thermal plume. The dislodged particles then are entrained in the human thermal plume that exists adjacent the human subject. The air in the human thermal plume, including the particles of interest that are dislodged from the clothing, are directed to trace detection system 430 for analysis. The EntryScan trace detection system, developed by GE Infrastructure Security, as well as the system described in U.S. Pat. No. 6,480,122, are such systems that could be modified in accordance with the teachings of the present invention to implement multi-sensor inspection system 400.

During operation, a person maybe instructed to enter passage 425. Visual signals or voice prompts may be used to instruct the person to remain in the passage for the duration of the inspection process, which is typically about 5-10 seconds. The jets may then fire sequentially from bottom to top. More particularly, the four lower tier jets may fire simultaneously for about 50 ms. There then may be a pause of about 100 ms, and the four jets in the second tier will fire for about 50 ms. This process will continue until the four jets in the top tier have fired. Particles displaced by the jets will be entrained in the human thermal plume and will flow naturally upward through the hood-shaped ceiling 420.

Concurrently or substantially concurrently with the firing of the air jets, QR inspection system 300 may also operate to inspect the lower extremities of the person. Specifically, the inspected person may be scanned to determine the presence of a target substance or object, such as an explosive, contraband, an illegal drug, a controlled substance, or conductive object using any of the techniques previously described.

Multi-sensor detection system 400 provides a synergistic combination of QR and trace detection systems to thoroughly inspect persons for items of interest. By operating both the QR and trace detection systems concurrently, the amount of time to inspect a person may be minimized as compared to sequentially inspecting a person with such sensors. However, if desired, the QR and trace detection system may be alternatively designed so that one system first inspects the person (either the QR or the trace detector). Once this system has completed the inspection process, then the other system performs its inspection process.

System 400 may be configured to alarm if either QR sensor 25 or trace detector system 430 meets or exceeds some predetermined measuring threshold. Alternatively, system 400 may utilize data obtained from the QR sensor and detector 430 to collectively render an alarm decision based upon some type of inspection logic. Another benefit provided by system 400 is that the functionality of two different inspection systems can be essentially integrated so that they collectively occupy approximately the same physical footprint. This is especially important in applications such as airport screening checkpoints which have specific space requirements with regard to the size of the screening equipment.

Multi-sensor detection system 400 is shown implementing QR sensor 25, but any of the QR sensors or other inductive sensors disclosed herein may alternatively be used. It is to be further understood that the various QR sensor systems provided herein may be used in conjunction with other inspection modalities. For example, in accordance with alternative embodiments, portal detection system 405 may be alternatively configured with other types of sensors such as, for example, an additional NQR sensor, a biological agent sensor, a chemical agent sensor, a metal detector, an x-ray system, a radiation detector, and the like.

Figure 16:
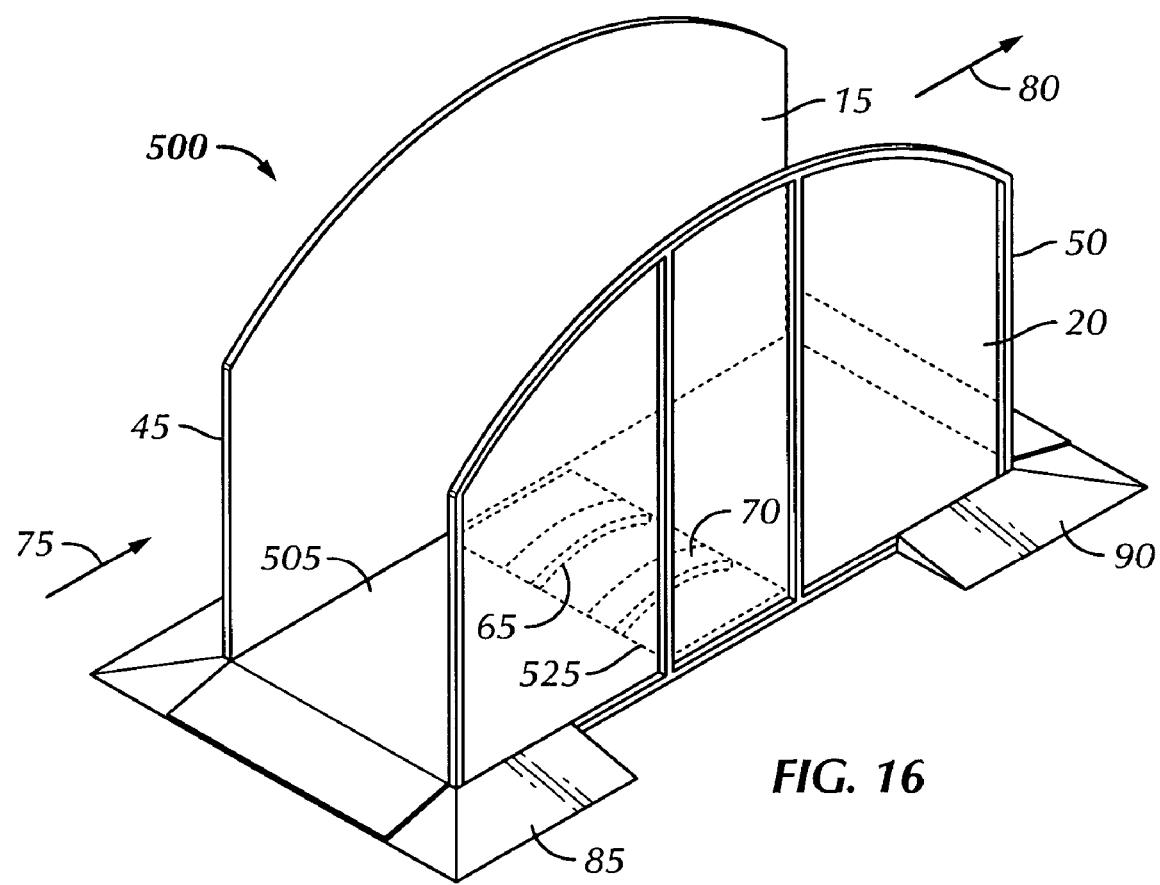
FIGS. 16, 17, and 18 are perspective, side-, and end-views, respectively, of an inspection system in accordance with an alternative embodiment of the present invention.
Figure 17:
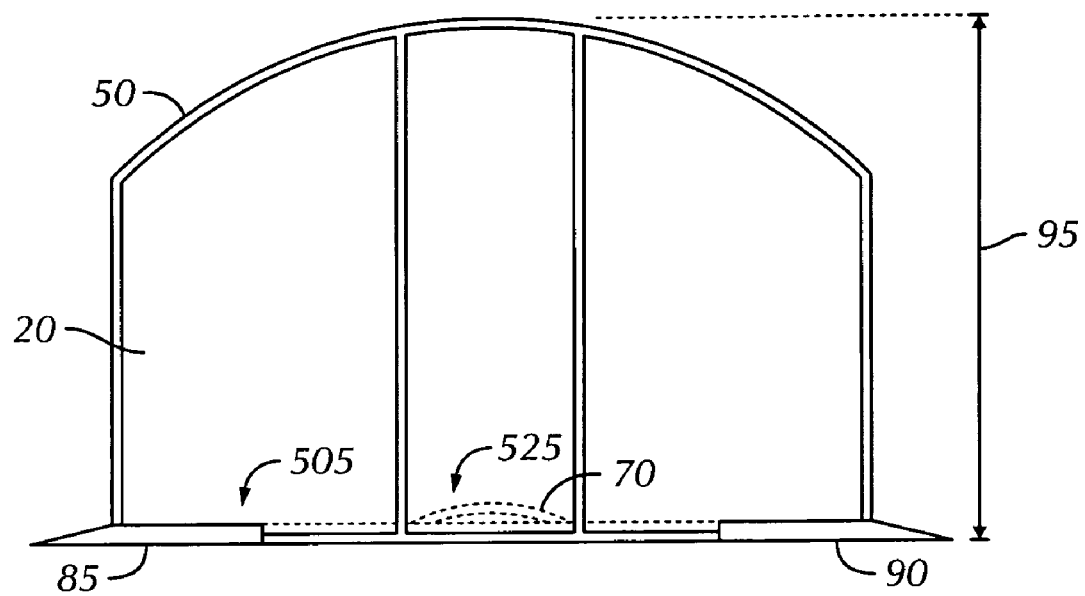
Figure 18:
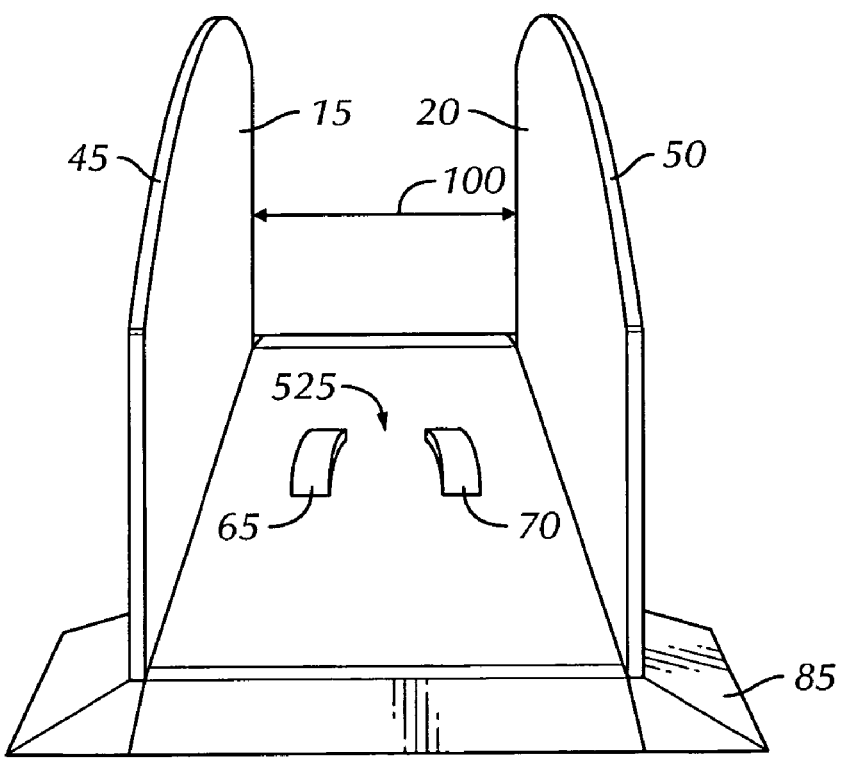

FIGS. 16, 17, and 18 are perspective, side, and end-views, respectively, of inspection system 500. Similar to other embodiments, inspection system 500 includes walls 15 and 20, and an inductive sensor 525 positioned within a walkway defined by the walls. As before, the inductive sensor is shown implemented as a QR sensor, but other types of inductive sensors may alternatively be used.

In contrast to the inclined ramp arrangement of the inspection system of FIGS. 1-3, system 500 includes floor 505, which defines a substantially flat walkway between walls 15 and 20. In accordance with the illustrated embodiment, QR sensor 525 includes current branches 65 and 70 which protrude from the floor of the inspection system. The protruding current branches do not require a recessed sensor housing. In general, the current branches of QR sensor 525 operate in a manner similar to that described above. However, QR sensor 525 provides additional functionality which will be described in more detail below.

Electromagnetic shielding for the inspection system may be accomplished by electrically connecting floor 505 with left and right walls 15 and 20. Each of these components of the shield may be formed from a suitably conductive material such as aluminum or copper. The left and right walls may also be welded to the floor component, or secured using any of the previously described techniques. If desired, the left and right walls, the floor, and the QR sensor may be covered with non-conducive materials such as wood, plastic, fabric, fiberglass, and the like.

During a typical inspection process, a person enters the system at entrance 75 and stands adjacent to the protruding current branches 65 and 70. The person may stand with their left foot positioned adjacent to current branch 65 and their right foot positioned adjacent to right current branch 70. QR sensor 525 then performs an inspection process using any of the previously described techniques to detect a target substance or object. Since the inspected person places each foot adjacent to, not on top of, a respective current branch, these current branches may be have a width that is substantially smaller than that utilized in other embodiments.

Figure 19:
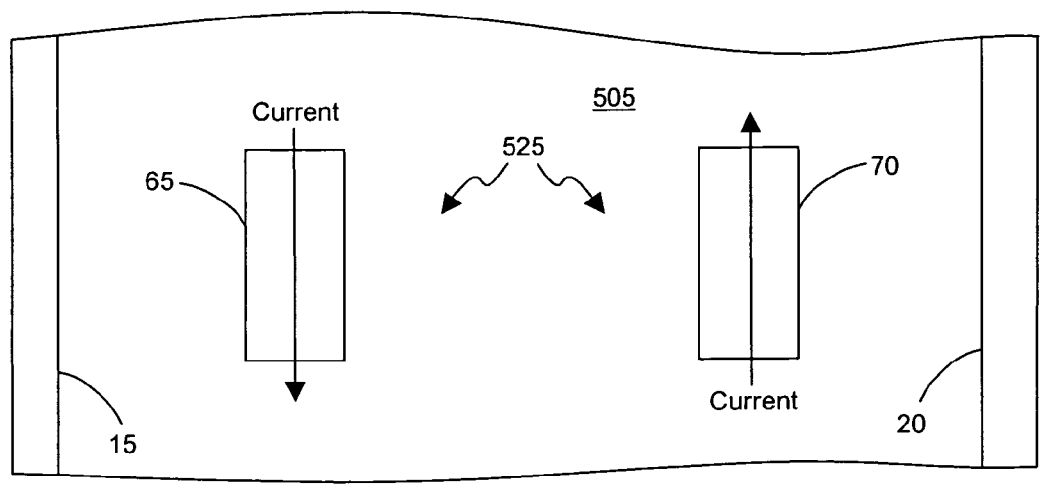
FIG. 19 is a top-view of a portion of the inspection system of FIGS. 16-18, showing the relative positioning of the left and right current branches.

FIG. 19 is a top view of a portion of inspection system 500, showing the relative positioning of left and right current branches 65 and 70. Similar to other embodiments, current branches 65 and 70 have anti-symmetric current flow.

Figure 20:
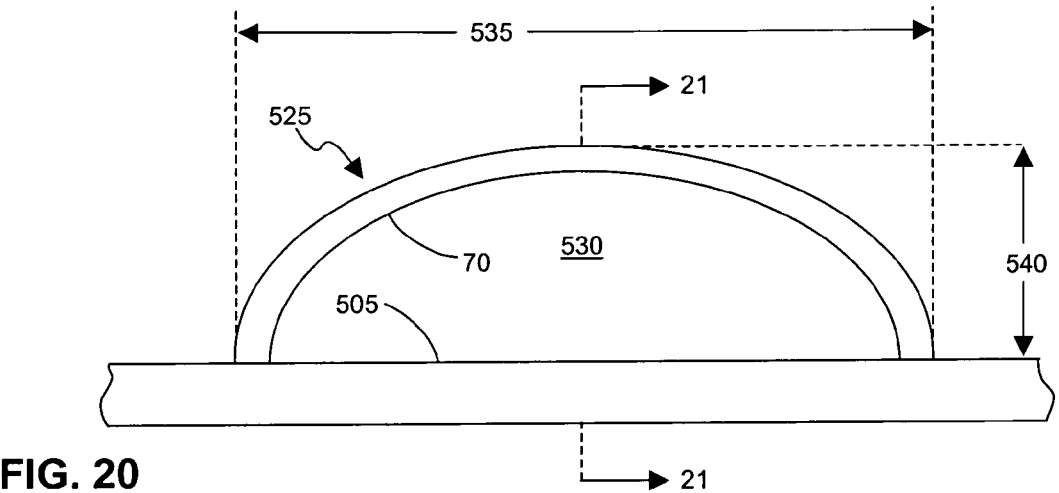
FIG. 20 is a side-view of the inductive sensor shown in FIGS. 16-18.

FIG. 20 is a side view of QR sensor 525, which is in electrical communication with floor 505. Only right current branch 70 is visible in this figure, but left current branch 65 may be similarly dimensioned and positioned. The right current branch is shown having a generally arcuate shape which forms gap 530. The gap is defined by the region between the bottom of the current branch and the top of floor 505. The current branch has length 535 and height 540. No particular length or height is required, but in general, the length of the current branches is such that they are slightly longer than the object or specimen being inspected. Using a typical walkthrough inspection station as an example, the left and right current branches may each have a length of about 12-24 inches, and an overall height of about ½-6 inches, or more.

Figure 21:
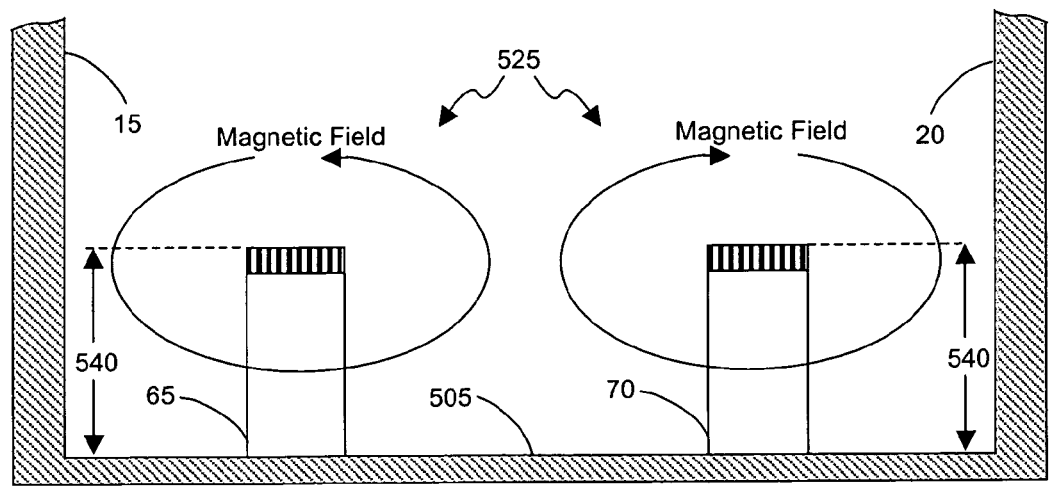
FIG. 21 is a partial cross-sectional view of the inspection system of FIGS. 16-18.

FIG. 21 is a partial cross-sectional view of QR inspection system 500, showing QR sensor 525 in electrical communication with floor 505. The left and right current branches 65 and 70 are shown producing counter-directed magnetic fields which individually circulate about their respective current branches. In other embodiments, a recess was formed in the floor of the inspection system to form a gap which allowed the magnetic fields to circulate. Such a recess is not necessary for system 500. Instead, the left and right current branches may be structured so that that they each form gap 530, which defines a non-conductive region between the current branch and floor 505. This non-conductive gap permits the magnetic fields to circulate about their respective current branches.

Another benefit provided by system 500 is that the inspection of a correspondingly higher location of the lower extremities of the inspected person may be accomplished. This is because the left and right current branches protrude from the floor of the inspection system, thus allowing the generated magnetic fields to engage the inspected person at a location which is further from the floor of the inspection station.

Figure 22:
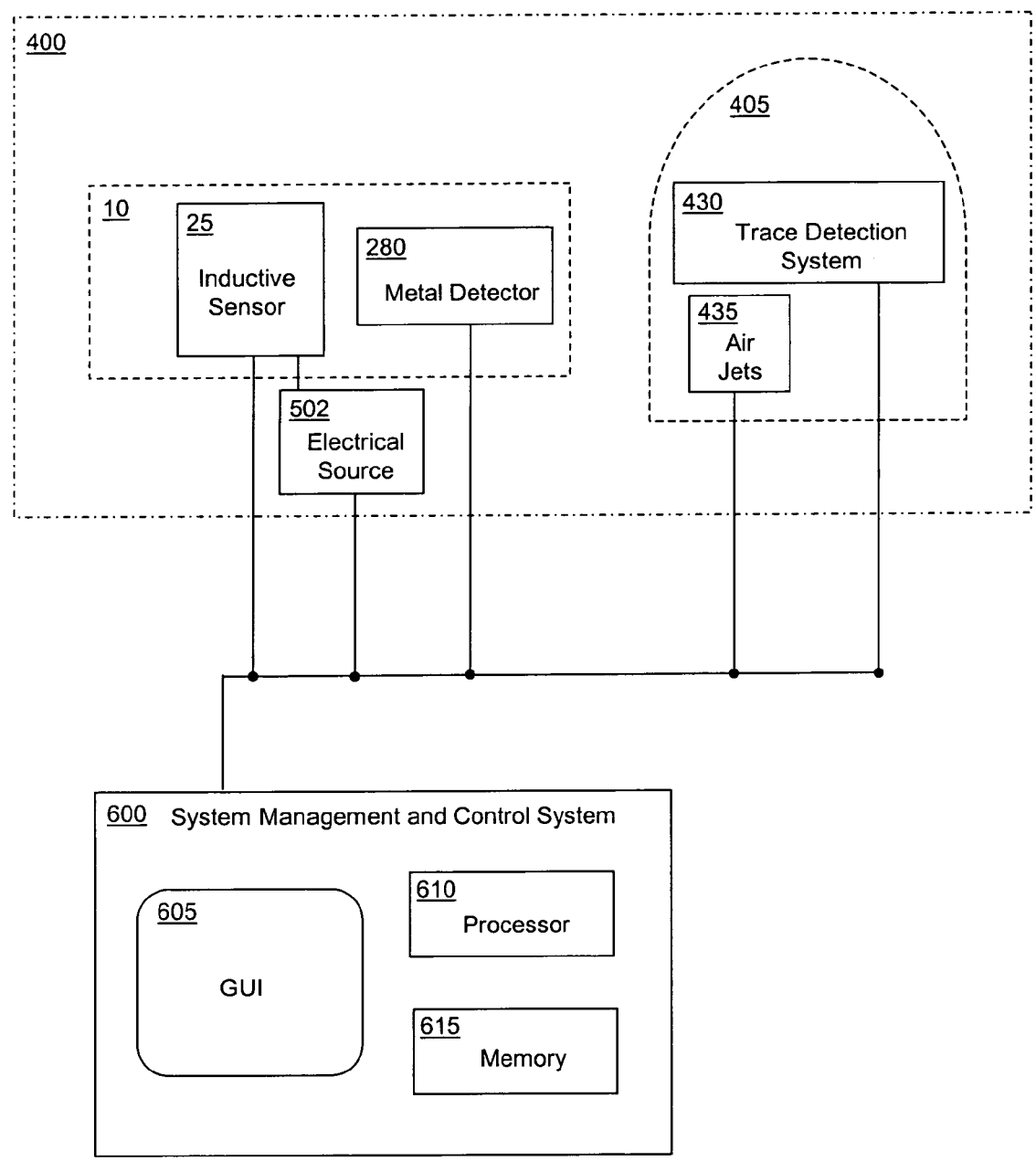
FIG. 22 is block diagram of a system which may be implemented to control, manage, operate, and monitor, the various inspection and detection systems disclosed herein.

FIG. 22 is block diagram of system 600, which may be implemented to control, manage, operate, and monitor, the various components associated with multi-sensor 400. Note that description of system 600 will be made with reference to metal detector 280, trace detection system 430, and air jets 435, which are all optional components. In addition, this figure will be described with reference to inspection system 10, but such description applies equally to the other inspection systems and various inductive sensors presented herein.

System 600 is shown having a graphical user interface 605, processor 610, and memory 615. The processor may be implemented using any suitable computational device that provides the necessary control, monitoring, and data analysis of the various systems and components associated with the various inspection and detector systems, including electrical source 502.

In general, processor 610 may be a specific or general purpose computer such as a personal computer having an operating system such as DOS, Windows, OS/2 or Linux; Macintosh computers; computers having JAVA OS as the operating system; graphical workstations such as the computers of Sun Microsystems and Silicon Graphics, and other computers having some version of the UNIX operating system such as AIX or SOLARIS of Sun Microsystems; or any other known and available operating system, or any device including, but not limited to, laptops and hand-held computers. Graphical user interface 605 may be any suitable display device operable with any of the computing devices described herein and may comprise a display such as an LCD, LED, CRT, plasma monitor, and the like.

The communication link between system 600 and the various inspection and detector systems may be implemented using any suitable technique that supports the transfer of data and necessary signaling for operational control of the various components (for example, inductive sensor 25, metal detector 280, trace detection system 430, air jets 435) of the multi-sensor inspection system. The communication link may be implemented using conventional communication technologies such as UTP, Ethernet, coaxial cables, serial or parallel cables, and optical fibers, among others. Although the use of wireless communication technologies is possible, they are typically not utilized since they may not provide the necessary level of security required by many applications such as airport baggage screening systems.

In some implementations, system 600 is physically configured in close physical proximity to the inspection system, but system 600 may be remotely implemented if so desired. Remote implementations may be accomplished by configuring system 600 and the inspection system with a suitably secure network link that comprises anything from a dedicated connection, to a local area network (LAN), to a wide area network (WAN), to a metropolitan area network (MAN), or even to the Internet.

The various methods and processes described herein may be implemented in a computer-readable medium using, for example, computer software, hardware, or some combination thereof. For a hardware implementation, the embodiments described herein may performed by processor 610, which may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a selective combination thereof.

For a software implementation, the embodiments described herein may be implemented with separate software modules, such as procedures, functions, and the like, each of which perform one or more of the functions and operations described herein. The software codes can be implemented with a software application written in any suitable programming language and may be stored in a memory unit (for example, memory 615), and executed by a processor (for example, processor 610). The memory unit may be implemented within the processor or external to the processor, in which case it can be communicatively coupled to the processor using known communication techniques. The memory unit shown in FIG. 22 may be implemented using any type (or combination) of suitable volatile and non-volatile memory or storage devices including random access memory (RAM), static random access memory (SRAM), electrically erasable programmable read-only memory (EEPROM), erasable programmable read-only memory (EPROM), programmable read-only memory (PROM), read-only memory (ROM), magnetic memory, flash memory, magnetic or optical disk, or other similar or effective memory or data storage device.

While the invention has been described in detail with reference to disclosed embodiments, various modifications within the scope of the invention will be apparent to those of ordinary skill in this technological field. It is to be appreciated that features described with respect to one embodiment typically may be applied to other embodiments. Therefore, the invention properly is to be construed only with reference to the claims.

What is claimed is:

1. An inspection system, comprising:
   an electromagnetic shield comprising electrically conductive sidewalls spaced from one another, and a conductive third wall electrically coupled to said sidewalls; and
   an inductive sensor positioned within said electromagnetic shield, said inductive sensor comprising at least two current branches positioned on opposing sides of a medial plane of said electromagnetic shield, said current branches having anti-symmetric current flow.

2. The inspection system according to claim 1, wherein said third wall comprises a recessed housing sized to receive at least a portion of said inductive sensor, wherein a non-conductive gap is formed between said inductive sensor and a surface of said housing.

3. The inspection system according to claim 2, wherein said current branches are electrically coupled to said third wall.

4. The inspection system according to claim 1, wherein said current branches protrude from said third wall to individually form a non-conductive gap between each of said current branches and said third wall.

5. The inspection system according to claim 1, wherein each of said current branches comprise an upper conductive element which is separated by a non-conductive gap from a lower conductive element; wherein
   a first conducting balance wire electrically couples said upper conductive element of a first branch of said current branches to said lower conductive element of a second branch of said current branches; and wherein
   a second conducting balance wire electrically couples said lower conductive element of said first branch to said upper conductive element of said second branch.

6. The inspection system according to claim 5, said inductive sensor further comprising:
   a first capacitor electrically coupled to said upper and lower conductive elements of said first branch; and
   a second capacitor electrically coupled to said upper and lower conductive elements of said second branch, said first and second capacitors forming a resonant circuit.

7. The inspection system according to claim 1, further comprising:

an electrical source providing electrical excitation to said inductive sensor, said electrical excitation causing:
a first magnetic field to circulate wound a first branch of said current branches, said electrical excitation further causing:
a second magnetic field to circulate wound a second branch of said current branches in a direction which is substantially opposite to said second magnetic field.

8. The inspection system according to claim 1, said system further comprising:
a radio frequency (RF) subsystem comprising a variable frequency RF source in communication with said inductive sensor, said RF source providing RF excitation signals at a frequency generally corresponding to predetermined, characteristic nuclear quadrupole resonant (NQR) frequency of a target substance, said RF excitation signals being applied to a specimen located within said electromagnetic shield, said inductive sensor functioning as a pickup coil for NQR signals from said specimen and providing an NQR output signal.

9. The inspection system according to claim 1, wherein said inductive sensor provides electrical excitation to a specimen positioned within said electromagnetic shield, wherein said electrical excitation causes a response indicative of the presence of an explosive substance.

10. The inspection system according to claim 1, wherein said inductive sensor provides electrical excitation to a specimen positioned within said electromagnetic shield, wherein said electrical excitation causes a response indicative of the presence of a conductive object.

11. The inspection system according to claim 1, said system further comprising:
a metal detection sensor positioned within said electromagnetic shield, said metal detection sensor for detecting conductive objects located within said electromagnetic shield.

12. The inspection system according to claim 1, wherein said inductive sensor is a nuclear quadrupolar resonant (NQR) sensor.

13. The inspection system according to claim 12, wherein said nuclear quadrupolar resonant (NQR) sensor comprises a sheet coil.

14. The inspection system according to claim 12, wherein said nuclear quadrupolar resonant (NQR) sensor comprises a tube array coil.

15. The inspection system according to claim 1, wherein said inductive sensor is a nuclear magnetic resonance (NMR) sensor.

16. The inspection system according to claim 1, wherein said inductive sensor is a metal detection sensor.

17. The inspection system according to claim 1, wherein current flow of said current branches is substantially parallel to said sidewalls.

18. An inspection system, comprising:
an electromagnetic shield comprising electrically conductive sidewalls spaced from one another, and a conductive third wall electrically coupled to said sidewalls; and
an inductive sensor positioned within said electromagnetic shield, said inductive sensor comprising:
a plurality of current branches positioned on a first side of a medial plane of said electromagnetic shield; and
a plurality of current branches positioned on an opposing second side of said medial plane; wherein
at least one of said plurality of current branches positioned on said first side exhibits current flow in a first direction; and at least one of said plurality of current branches positioned on said second side exhibits current flow in a second direction which is anti-symmetric to said first direction.

19. The inspection system according to claim 18, wherein each of said plurality of current branches positioned on said first and second sides of said medial plane comprise an upper conductive element which is separated by a non-conductive gap from a lower conductive element; wherein
a first plurality of conducting balance wires individually electrically couple each of said upper conductive elements positioned on said first side with a separate one of said lower conductive elements positioned on said second side; and
a second plurality of conducting balance wires which individually electrically couple each of said lower conductive elements positioned on said first side with a separate one of said upper conductive elements positioned on said second side.

20. The inspection system according to claim 19, said inductive sensor further comprising:
a separate first capacitor electrically coupled to each of said upper and lower conductive elements of said first branch; and
a separate second capacitor electrically coupled to upper and lower conductive element of said second branch, said first and second capacitors collectively forming a resonant circuit.

21. The inspection system according to claim 18, wherein:
at least two of said current branches positioned on said first side exhibit current flow in said first direction; and wherein
at least two of said current branches positioned on said second side exhibit current flow in said second direction.

22. The inspection system according to claim 21, further comprising:
an electrical source providing electrical excitation to said inductive sensor, said electrical excitation causing:
a first magnetic field to circulate around said plurality of current branches positioned on said first side, said electrical excitation further causing:
a second magnetic field to circulate around said plurality of current branches positioned on said second side in a direction which is substantially opposite to said first magnetic field.

23. The inspection system according to claim 18, wherein:
one of said plurality of current branches positioned on said first side exhibits current flow in said first direction, and another one of said plurality of current branches positioned on said first side exhibits current flow in said second direction; and wherein
one of said plurality of current branches positioned on said second side exhibits current flow in said first direction, and another one of said plurality of current branches positioned on said second side exhibits current flow in said second direction.

24. The inspection system according to claim 23, further comprising:
an electrical source providing electrical excitation to said inductive sensor, said electrical excitation causing:
a magnetic field to circulate around each of said plurality of current branches positioned on said first side, wherein adjacent current branches on said first side exhibit magnetic fields which circulate in substantially opposite directions, said electrical excitation further causing:

a magnetic field to circulate around each of said plurality of current branches positioned on said second side, wherein adjacent current branches on said second side exhibit magnetic fields which circulate in substantially opposite directions.

25. A method for inspecting a specimen within a three-walled electromagnetic shield, said method comprising:

causing a first magnetic field to circulate around a first current branch of an inductive sensor; and causing a second magnetic field to circulate around a second branch of said inductive sensor in a direction which is substantially opposite to said first magnetic field.

26. A method for inspecting a specimen within a three-walled electromagnetic shield, said method comprising:

causing a first magnetic field to circulate around a plurality of current branches positioned on a first side of a medial plane of said electromagnetic shield; and causing a second magnetic field to circulate around a plurality of current branches positioned on a second side of said medial plane of said electromagnetic shield in a direction which is substantially opposite to said first magnetic field.

27. A method for inspecting a specimen within a three-walled electromagnetic shield, said method comprising:

causing a magnetic field to circulate around each of a plurality of current branches positioned on a first side of a medial plane of said electromagnetic shield;

causing adjacent current branches on said first side to exhibit magnetic fields which circulate in substantially opposite directions;

causing a magnetic field to circulate around each of a plurality of current branches positioned on a second side of said medial plane of said electromagnetic shield; and causing adjacent current branches on said second side to exhibit magnetic fields which circulate in substantially opposite directions.

28. A method for inspecting a subject within a three-walled electromagnetic shield, said method comprising:

receiving air flowing adjacent to a subject present within said electromagnetic shield;

inspecting said air for items of interest; and inspecting lower extremities of said subject for items of interest using an inductive sensor positioned within said electromagnetic shield.

* * * * *